United States Patent [19]
Watanabe et al.

[11] Patent Number: 6,147,249
[45] Date of Patent: Nov. 14, 2000

[54] ESTER COMPOUNDS, POLYMERS, RESIST COMPOSITION AND PATTERNING PROCESS

[75] Inventors: Takeru Watanabe; Takeshi Kinsho; Tsunehiro Nishi; Mutsuo Nakashima; Koji Hasegawa; Jun Hatakeyama, all of Niigata-ken, Japan

[73] Assignee: Shin-Etsu Chemical Co., Ltd., Tokyo, Japan

[21] Appl. No.: 09/307,767

[22] Filed: May 10, 1999

[30] Foreign Application Priority Data

| May 11, 1998 | [JP] | Japan | ................................. 10-145080 |
| Oct. 14, 1998 | [JP] | Japan | ................................. 10-292575 |

[51] Int. Cl.$^7$ .................................................. C07C 69/74
[52] U.S. Cl. ........................... 560/120; 560/118; 526/281
[58] Field of Search ............................ 526/281; 560/120, 560/118

[56] References Cited

U.S. PATENT DOCUMENTS

| 4,491,628 | 1/1985 | Ito et al. . | |
| 4,603,101 | 7/1986 | Crivello . | |
| 5,053,471 | 10/1991 | Goto et al. | ............................... 526/281 |
| 5,069,997 | 12/1991 | Schwalm et al. . | |
| 5,585,222 | 12/1996 | Kaimoto et al. . | |

OTHER PUBLICATIONS

Allen et al., Single Layer Resists With Enhanced Etch Resistance for 193 nm Lithography, *Journal of Photopolymer Science and Technology*, vol. 7, No. 3, pp. 507–516 (1994).

English Abstract for JP–A 88367/1993.
English Abstract for JP–A 215661/1992.

*Primary Examiner*—Paul J. Killos
*Assistant Examiner*—Taylor V Oh
*Attorney, Agent, or Firm*—Millen, White, Zelano & Branigan, P.C.

[57] ABSTRACT

A novel ester compound having an alkylcycloalkyl or alkylcycloalkenyl group as the protective group is provided as well as a polymer comprising units of the ester compound. The polymer is used as a base resin to formulate a resist composition having a higher sensitivity, resolution and etching resistance than conventional resist compositions.

20 Claims, No Drawings

ESTER COMPOUNDS, POLYMERS, RESIST COMPOSITION AND PATTERNING PROCESS

BACKGROUND OF THE INVENTION

1. Field of the Invention

The present invention relates to (1) a novel ester compound, (2) a polymer comprising units of the ester compound which is blended as a base resin to formulate a resist composition having a high sensitivity, resolution and etching resistance, and in particular, suitable as micropatterning material for VLSI fabrication, (3) a method for preparing the polymer, (4) a resist composition comprising the polymer, and (5) a patterning process using the resist composition.

2. Prior Art

Deep-ultraviolet lithography, one of a number of recent efforts that are being made to achieve a finer pattern rule in the drive for higher integration and operating speeds in LSI devices, is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with a KrF excimer lasers, polyhydroxystyrene having a practical level of transmittance and etching resistance is, in fact, a standard base resin. For resist materials for use with a ArF excimer lasers, polyacrylic or polymethacrylic acid derivatives and polymers comprising aliphatic cyclic compounds in the backbone are under investigation. In either case, the basic concept is that some or all of alkali soluble sites of alkali soluble resin are protected with acid labile or eliminatable groups. The overall performance of resist material is adjusted by a choice from among a variety of acid eliminatable protective groups.

Exemplary acid eliminatable protective groups include tert-butoxycarbonyl (JP-B 27660/1990), tert-butyl (JP-A 115440/1987 and J. Photopolym. Sci. Technol. 7 [3], 507 (1994)), 2-tetrahydropyranyl (JP-A 80515/1993 and 88367/1993), and 1-ethoxyethyl (JP-A 19847/1990 and 215661/1992). While it is desired to achieve a finer pattern rule, none of these acid eliminatable protective groups are deemed to exert satisfactory performance.

More particularly, tert-butoxycarbonyl and tert-butyl are extremely less reactive with acids so that a substantial quantity of energy radiation must be irradiated to generate a sufficient amount of acid in order to establish a difference in rate of dissolution before and after exposure. If a photoacid generator of the strong acid type is used, the exposure can be reduced to a relatively low level because reaction can proceed with a small amount of acid generated. However, in this event, the deactivation of the generated acid by airborne basic substances has a relatively large influence, giving rise to such problems as a T-top pattern. On the other hand, 2-tetrahydropyranyl and 1-ethoxyethyl are so reactive with acids that with the acid generated by exposure, elimination reaction may randomly proceed without a need for heat treatment, with the result that substantial dimensional changes occur between exposure and heat treatment/development. Where these groups are used as protective groups for carboxylic acid, they have a low dissolution inhibiting effect to alkali, resulting in a high rate of dissolution in unexposed areas and film thinning during development. If highly substituted polymers are used to avoid such inconvenience, there results an extreme drop of heat resistance. These resins fail to provide a difference in rate of dissolution before and after exposure, resulting in resist materials having a very low resolution.

SUMMARY OF THE INVENTION

Therefore, an object of the present invention is to provide (1) a novel ester compound capable of forming an acid-decomposable polymer, (2) a polymer which is blended as a base resin to formulate a resist composition having a higher sensitivity, resolution and etching resistance than conventional resist compositions, (3) a method for preparing the polymer, (4) a resist composition comprising the polymer as a base resin, and (5) a patterning process using the resist composition.

The inventor has found that a novel ester compound of the following general formula (1) obtained by the method to be described later is useful in preparing an acid-decomposable polymer; that a resist composition comprising as the base resin a novel polymer prepared from the ester compound to a weight average molecular weight of 1,000 to 500,000 has a high sensitivity, resolution and etching resistance; and that this resist composition lends itself to precise micropatterning.

In a first aspect, the invention provides an ester compound of the following general formula (1):

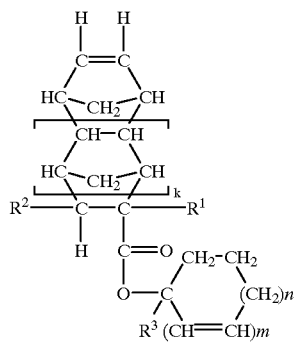

(1)

wherein $R^1$ is hydrogen, methyl or $CH_2CO_2R^4$; $R^2$ is hydrogen, methyl or $CO_2R^4$; $R^3$ is a straight, branched or cyclic alkyl group of 1 to 8 carbon atoms or a substituted or unsubstituted aryl group of 6 to 20 carbon atoms; $R^4$ is a straight, branched or cyclic alkyl group of 1 to 15 carbon atoms; k is equal to 0 or 1, m is equal to 0 or 1, n is equal to 0, 1, 2 or 3, and 2m+n is equal to 2 or 3.

In a second aspect, the invention provides a polymer comprising units of an ester compound of the following general formula (1a-1) or (1a-2) and having a weight average molecular weight of 1,000 to 500,000.

(1a-1)

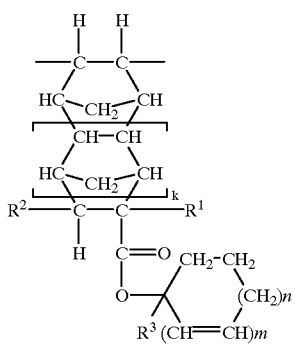

(1a-2)

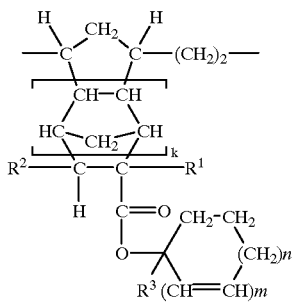

$R^1$, $R^2$, $R^3$, k, m, and n are as defined above.

The polymer may further comprises recurring units of at least one of the following formulae (2a) to (10a):

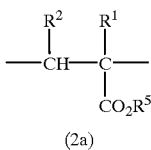  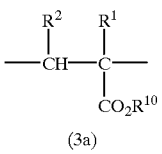

(2a)  (3a)

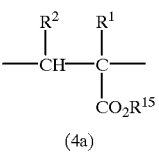  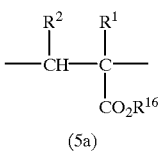

(4a)  (5a)

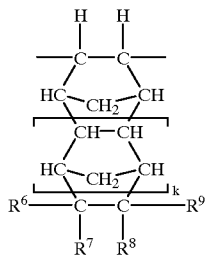  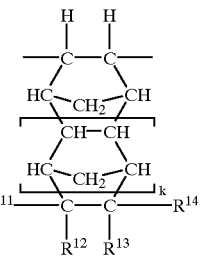

(6a-1)  (7a-1)

-continued

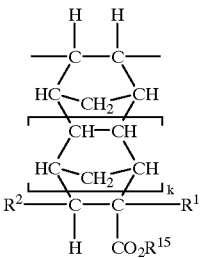  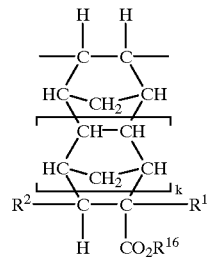

(8a-1)  (9a-1)

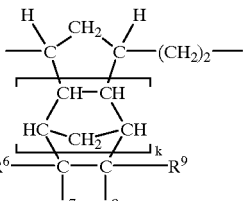  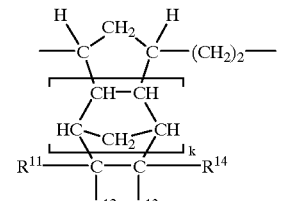

(6a-2)  (7a-2)

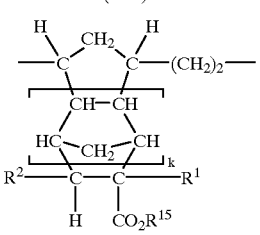  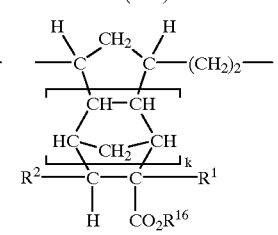

(8a-2)  (9a-2)

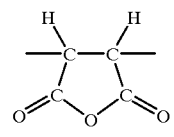

(10a)

wherein $R^1$ and $R^2$ are as defined above; $R^5$ is hydrogen or a monovalent hydrocarbon group of 1 to 15 carbon atoms containing a carboxyl or hydroxyl group; at least one of $R^6$ to $R^9$ represents a monovalent hydrocarbon group of 1 to 15 carbon atoms containing a carboxyl or hydroxyl group, and the remaining of $R^6$ to $R^9$ independently represent hydrogen or a straight, branched or cyclic alkyl group of 1 to 15 carbon atoms, or $R^6$ to $R^9$, taken together, may form a ring with the proviso that at least one of $R^6$ to $R^9$ represents a divalent hydrocarbon group of 1 to 15 carbon atoms containing a carboxyl or hydroxyl group, and the remaining of R6 to $R^9$ independently represent a straight, branched or cyclic alkylene group of 1 to 15 carbon atoms; $R^{10}$ is a monovalent hydrocarbon group of 3 to 15 carbon atoms containing a —$CO_2$— partial structure; at least one of $R^{11}$ to $R^{14}$ represents a monovalent hydrocarbon group of 2 to 15 carbon atoms containing a —$CO_2$— partial structure, and the remaining of $R^{11}$ to $R^{14}$ independently represent hydrogen or a straight, branched or cyclic alkyl group of 1 to 15 carbon atoms, or $R^{11}$ to $R^{14}$, taken together, may form a ring with the proviso that at least one of $R^{11}$ to $R^{14}$ represents a divalent hydrocarbon group of 1 to 15 carbon atoms containing a —$CO_2$— partial structure, and the remaining of $R^{11}$ to $R^{14}$ independently represent a straight, branched or cyclic alkylene group of 1 to 15 carbon atoms; $R^{15}$ is a polycyclic hydrocarbon group of 7 to 15 carbon atoms or an alkyl group containing a polycyclic hydrocarbon group; $R^{16}$ is an acid labile group, and k is equal to 0 or 1.

In a third aspect, the invention provides a method for preparing a polymer comprising the step of effecting radical polymerization, anionic polymerization or coordination polymerization between an ester compound of formula (1) and another compound having a carbon-to-carbon double bond.

In a fourth aspect, the invention provides a resist composition comprising the polymer defined above, and preferably a photoacid generator, and an organic solvent.

In a fifth aspect, the invention provides a process for forming a pattern, comprising the steps of applying the resist composition defined above onto a substrate to form a coating; heat treating the coating and exposing the coating to high energy radiation or electron radiation through a photomask; optionally heat treating the exposed coating, and developing the coating with a developer.

The ester compound of formula (1) and the polymer comprising units of formula (1a-1) or (1a-2) employ alkylcycloalkyl or alkylcycloalkenyl groups of the following formula (1b):

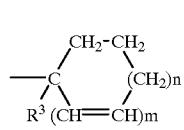

(1b)

wherein $R^3$, m and n are as defined above, as the acid-eliminatable protective group, thereby overcoming the problems including the tert-butoxycarbonyl and tert-butyl groups having low reactivity with acid as well as the 2-tetrahydropyranyl and 1-ethoxyethyl groups having too high reactivity with acid and low resistance to alkaline developers.

Under acidic conditions, the ester compound of formula (1) decomposes to generate a carboxylic acid while forming an olefin compound. This mechanism itself is just the same as the acidolysis of tertiary alkyl esters such as tert-butyl esters, but the rate of progress substantially differs. Specifically, the acidolysis of tertiary alkyl esters proceeds in such a way that a carboxylic acid and a tertiary alkyl cation first form and then the cation is extinguished by proton release, to form an olefin compound, reaching the completion of reaction. The rate-determining step of this decomposition reaction is the later extinction of cation. In the case of the ester compound of formula (1), this step proceeds very fast probably because the alleviated distortion of the ring, the formation of a conjugated system and other factors provide a very powerful drive force. Moreover, the re-reactivity of the olefin generated is very low. These result in a greater acidolysis liability than other tertiary alkyl esters.

Since the ester compound of formula (1) is basically a tertiary alkyl ester, it does not allow for the infinite progress of decomposition between exposure and development and film thinning during development as found with 2-tetrahydropyranyl and 1-ethoxyethyl groups. Therefore, when a polymer comprising units of this ester compound is blended in a resist composition as the base resin, the resulting resist composition has a high dissolution contrast in the sense that unexposed areas have a very low rate of dissolution while areas having been irradiated with an appropriate dose of light quickly become alkali soluble, as well as a high sensitivity and high resolution. In addition, this polymer has a robust alicyclic skeleton in its backbone, exerting a very high etching resistance.

DETAILED DESCRIPTION OF THE INVENTION

Ester Compound

The novel ester compounds according to the first aspect of the invention are of the following general formula (1).

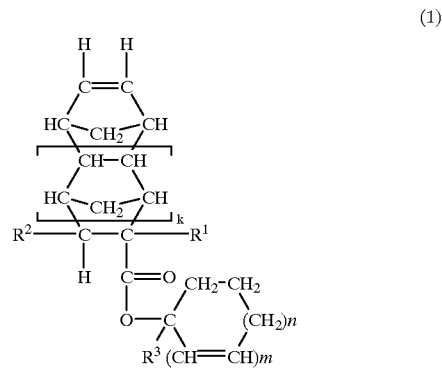

(1)

Herein, $R^1$ is hydrogen, methyl or $CH_2CO_2R^4$ wherein $R^4$ is illustrated later. $R^2$ is hydrogen, methyl or $CO_2R^4$. $R^3$ is a straight, branched or cyclic alkyl group of 1 to 8 carbon atoms or a substituted or unsubstituted aryl group of 6 to 20 carbon atoms. Illustrative examples of the straight, branched or cyclic alkyl group include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Illustrative examples of the substituted or unsubstituted aryl group include phenyl, methylphenyl, naphthyl, anthryl, phenanthryl, and pyrenyl. $R^4$ is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl. Letter k is equal to 0 or 1, m is equal to 0 or 1, n is equal to 0, 1, 2 or 3, and 2m+n is equal to 2 or 3.

Illustrative, non-limiting examples of the ester compound according to the invention are given below.

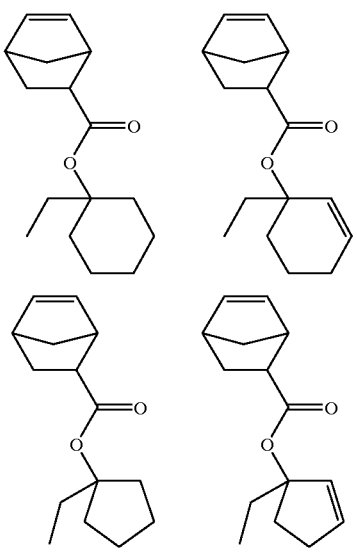

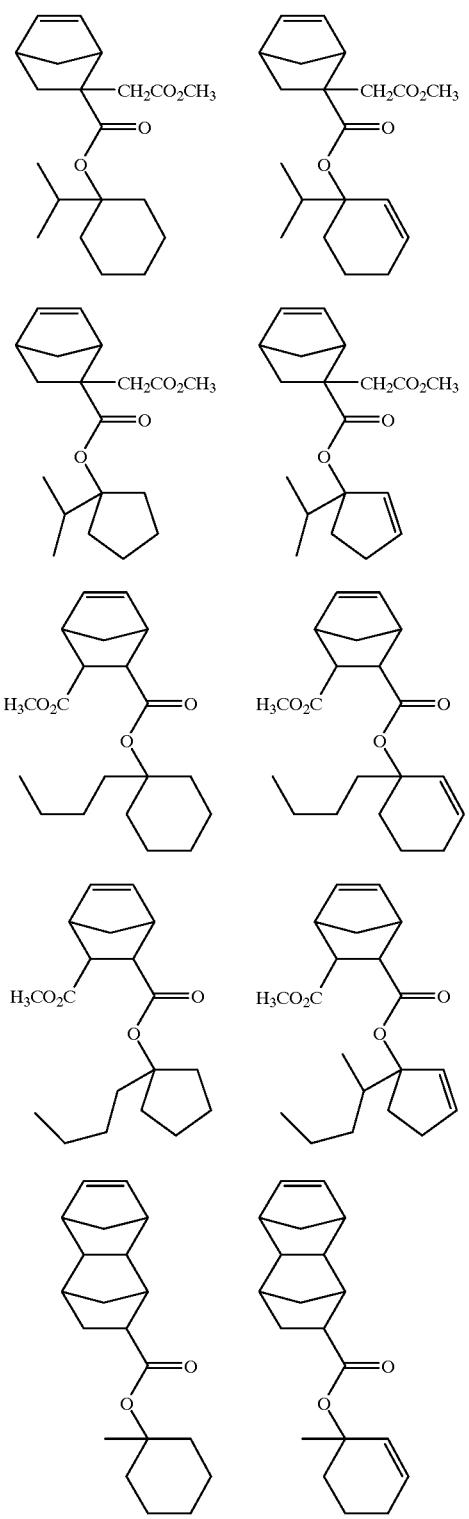

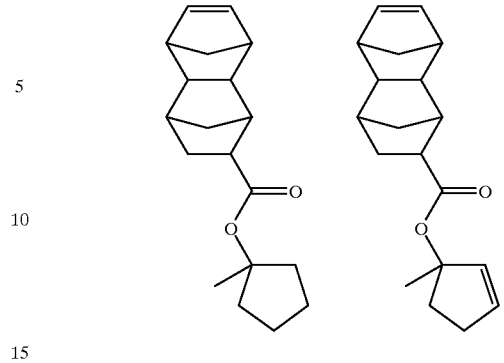

The ester compounds of the invention can be prepared, for example, by the following procedure although the invention is not limited thereto.

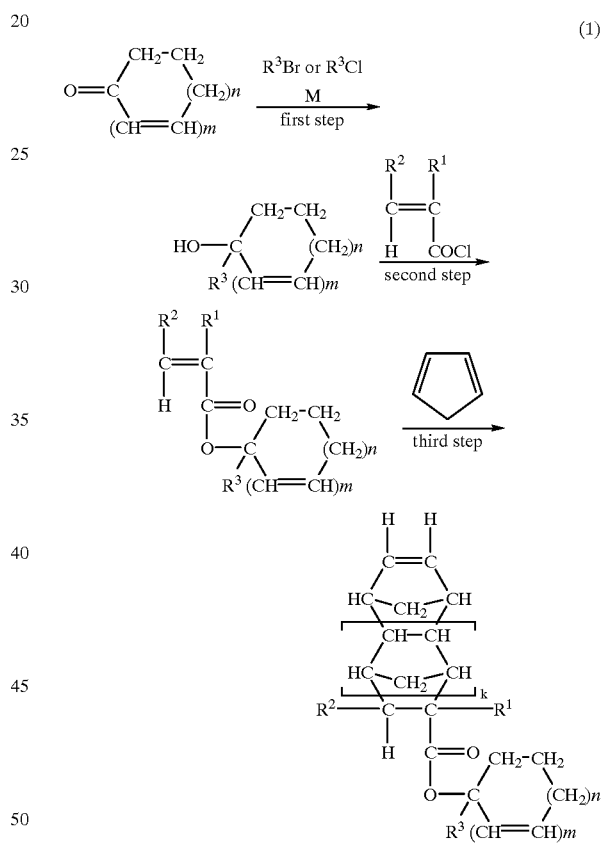

Herein, $R^1$, $R^2$, $R^3$, k, m, and n are as defined above, and M is a metal.

The first step is to effect nucleophilic addition reaction to the carbonyl of a cyclic ketone compound to convert it into a tertiary alcohol. Illustrative of this step are Grignard reaction and reaction using organic lithium compounds although the reaction involved in this step is not limited thereto. Reaction readily takes place under well-known conditions. Reaction is preferably carried out by mixing the reactants: a cyclic ketone compound and an alkyl halide or aryl halide with the metal M such as magnesium or lithium in a solvent such as tetrahydrofuran or diethyl ether and heating or cooling the reaction mixture if desired.

The second step is to convert the tertiary alcohol from the first step into an ester of an unsaturated acid. Reaction readily takes place under well-known conditions. Reaction is preferably carried out by mixing the reactants: the tertiary alcohol, a carboxylic acid halide (e.g., acrylic acid chloride or methacrylic acid chloride), and a base (e.g., triethylamine) in a solvent such as methylene chloride and cooling the reaction mixture if desired.

The third step is to construct an alicyclic skeleton through Diels-Alder reaction. Reaction readily takes place under well-known conditions. Reaction is preferably carried out by mixing the reactants: the unsaturated acid ester and cyclopentadiene in a solvent such as benzene or in a solventless system, optionally in the presence of a catalyst such as boron trifluoride, and heating or cooling the reaction mixture if desired.

Polymer

In the second aspect, the invention provides a polymer or high molecular weight compound comprising units of the following general formula (1a-1) or (1a-2) which are obtained using an ester compound of formula (1) as a monomer, and having a weight average molecular weight of 1,000 to 500,000, preferably 5,000 to 100,000.

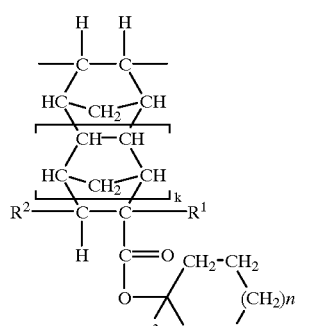

(1a-1)

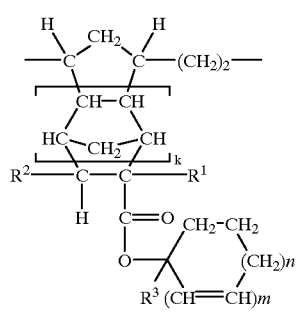

(1a-2)

Herein, $R^1$, $R^2$, $R^3$, k, m, and n are as defined above.

The polymer of the invention may further comprise recurring units of at least one type selected from recurring units of the following general formulae (2a) to (10a) which are obtained using monomers of the following general formulae (2) to (10).

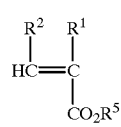

(2)

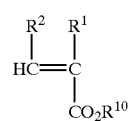

(3)

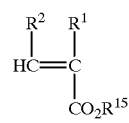

(4)

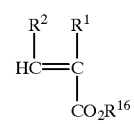

(5)

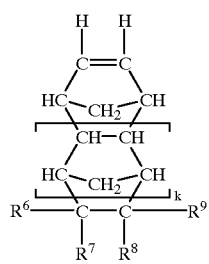

(6)

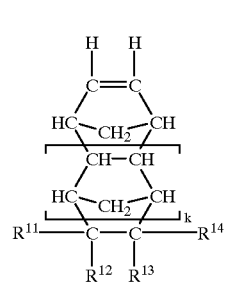

(7)

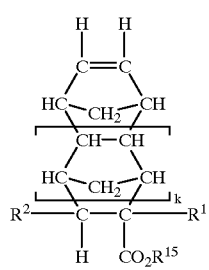

(8)

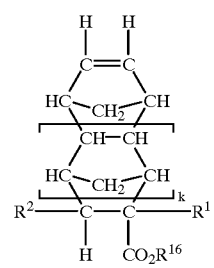 (9)
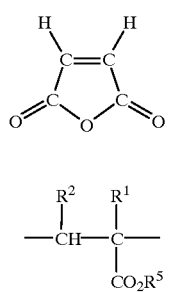 (10)
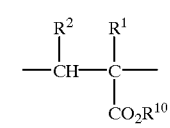 (2a)
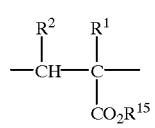 (3a)
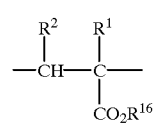 (4a)
(5a)
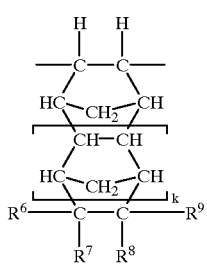 (6a-1)
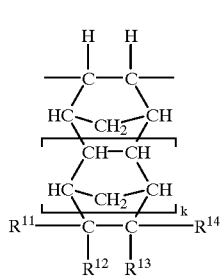 (7a-1)
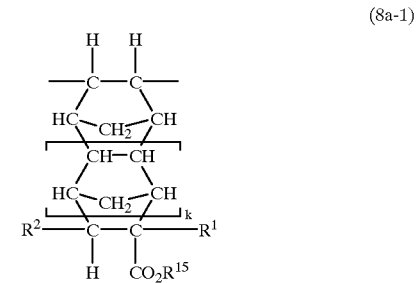 (8a-1)
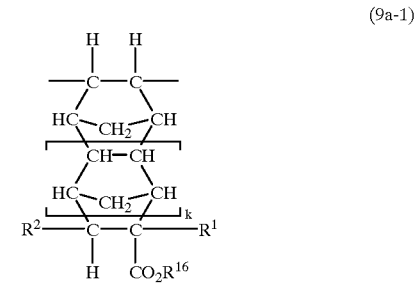 (9a-1)
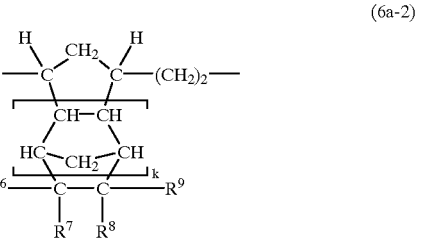 (6a-2)
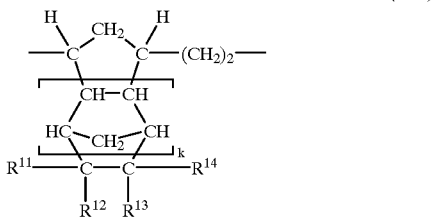 (7a-2)
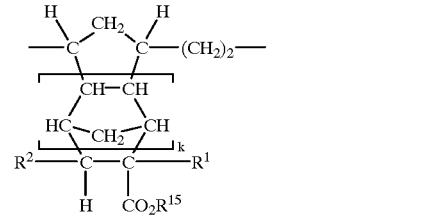 (8a-2)
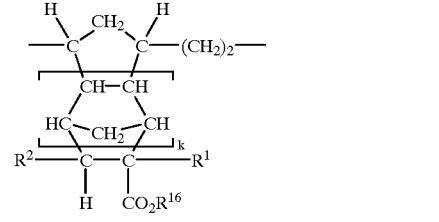 (9a-2)

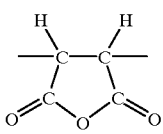
(10a)

In the above formulae, k is equal to 0 or 1. Then formulae (6a-1) to (9a-2) may also be represented by the following formulae (6a-1-1) to (9a-2-2).

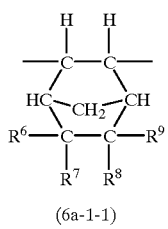 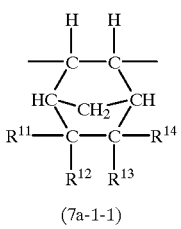
(6a-1-1)   (7a-1-1)

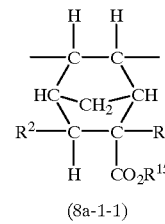 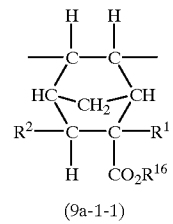
(8a-1-1)   (9a-1-1)

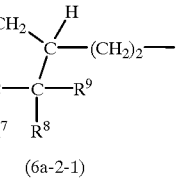 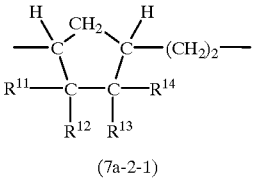
(6a-2-1)   (7a-2-1)

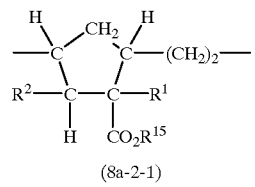 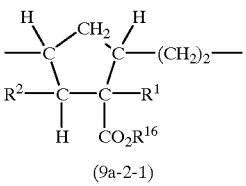
(8a-2-1)   (9a-2-1)

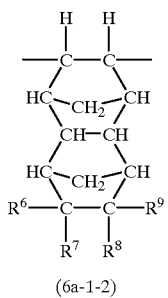 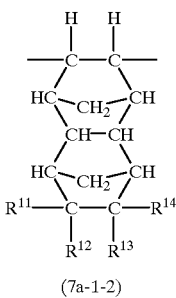
(6a-1-2)   (7a-1-2)

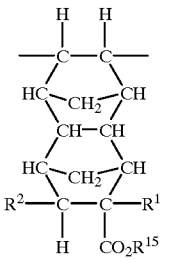 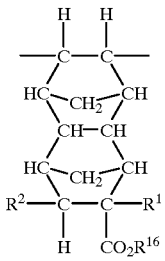
(8a-1-2)   (9a-1-2)

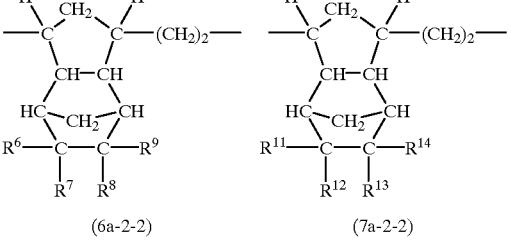
(6a-2-2)   (7a-2-2)

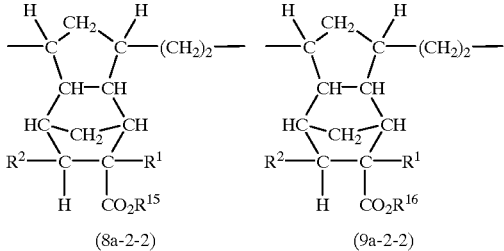
(8a-2-2)   (9a-2-2)

Herein, $R^1$ and $R^2$ are as defined above. $R^5$ is hydrogen or a monovalent hydrocarbon group of 1 to 15 carbon atoms having a carboxyl or hydroxyl group, for example, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, or hydroxyadamantyl. At least one of $R^6$ to $R^9$ is hydrogen or a monovalent hydrocarbon group of 1 to 15 carbon atoms having a carboxyl or hydroxyl group, while the remaining R's are independently hydrogen or straight, branched or cyclic alkyl groups of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^4$. $R^6$ to $R^9$, taken together, may form a ring, and in that event, at least one of $R^6$ to $R^9$ is a divalent hydrocarbon group of 1 to 15 carbon atoms having a carboxyl or hydroxyl group, while the remaining R's are independently straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^4$, with one hydrogen atom eliminated therefrom.

$R^{10}$ is a monovalent hydrocarbon group of 3 to 15 carbon atoms containing a —$CO_2$— partial structure, for example, 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl. At least one of $R^{11}$ to $R^{14}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. Examples of the monovalent hydrocarbon group of 2 to 15 carbon atoms containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^4$. $R^{11}$ to $R^{14}$, taken together, may form a ring, and in that event, at least one of $R^1$ to $R^{14}$ is a divalent hydrocarbon group of 1 to 15 carbon atoms containing a —$CO_2$— partial structure, while the remaining R's are independently straight, branched or cyclic alkylene groups of 1 to 15 carbon atoms. Examples of the divalent hydrocarbon group of 1 to 15 carbon atoms containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group containing a —$CO_2$— partial structure, with one hydrogen atom eliminated therefrom. Examples of the straight, branched or cyclic alkylene groups of 1 to 15 carbon atoms include the groups exemplified for $R^4$, with one hydrogen atom eliminated therefrom.

$R^{15}$ is a polycyclic hydrocarbon group having 7 to 15 carbon atoms or an alkyl group containing a polycyclic hydrocarbon group, for example, norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl. $R^{16}$ is an acid labile group. k is equal to 0 or 1.

Illustrative groups of the acid labile group represented by $R^{16}$ include groups of the following formulae (11) and (12), tertiary alkyl groups of 4 to 20 carbon atoms, preferably 4 to 15 carbon atoms, trialkylsilyl groups whose alkyls each have 1 to 6 carbon atoms, and oxoalkyl groups of 4 to 20 carbon atoms.

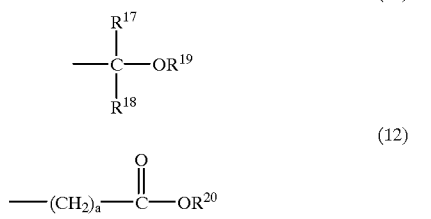

Herein, $R^{17}$ and $R^{18}$ each are hydrogen or a straight, branched or cyclic alkyl group of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl, and n-octyl. $R^{19}$ is a monovalent hydrocarbon group of 1 to 18 carbon atoms, preferably 1 to 10 carbon atoms, which may have a hetero atom such as an oxygen atom, for example, straight, branched or cyclic alkyl groups, in which some hydrogen atoms may be replaced by hydroxyl, alkoxy, oxo, amino, or alkylamino groups. More illustrative of the $R^{19}$ group are the substituted alkyl groups shown below.

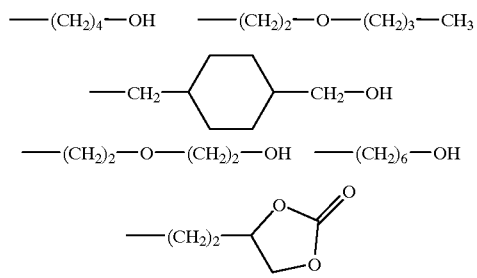

A pair of $R^{17}$ and $R^{18}$, $R^{17}$ and $R^{19}$, or $R^{18}$ and $R^{19}$, taken together, may form a ring. $R^{17}$, $R^{18}$ and $R^{19}$ each represent straight or branched alkylene groups of 1 to 8 carbon atoms, preferably 1 to 10 carbon atoms when they form a ring.

$R^{20}$ is a tertiary alkyl group of 4 to 20 carbon atoms, preferably 4 to 15 carbon atoms, trialkylsilyl group whose alkyls each have 1 to 6 carbon atoms, oxoalkyl group of 4 to 20 carbon atoms, or group of above formula (11). Letter a is an integer of 0 to 6.

Exemplary tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl. Exemplary trialkylsilyl groups are those whose alkyl groups each have 1 to 6 carbon atoms, such as trimethylsilyl, triethylsilyl and dimethyl-tert-butylsilyl. Examples of oxoalkyl groups include 3-oxocyclohexyl, 4-methyl-2-oxooxan-4-yl, and 5-methyl-2-oxooxolan-5-yl.

Of the acid labile groups of formula (11), straight and branched groups are illustrated below.

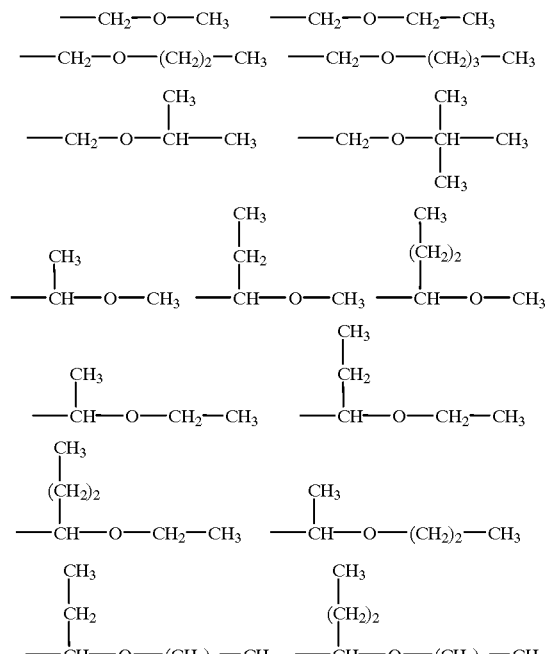

-continued

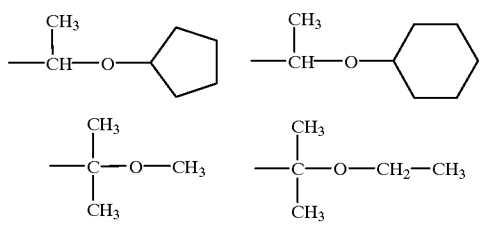

Of the acid labile groups of formula (11), cyclic groups are illustrated below.

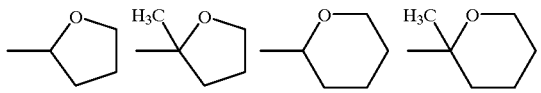

Illustrative examples of the acid labile group of formula (12) include tert-butoxycarbonyl, tert-butoxy-carbonylmethyl, tert-amyloxycarbonyl, tert-amyloxy-carbonylmethyl, 1,1-diethylpropyloxycarbonyl, 1,1-diethylpropyloxycarbonylmethyl, 1-ethylcyclopentyloxy-carbonyl, 1-ethylcyclopentyloxycarbonylmethyl, 1-ethyl-2-cyclopentenyloxycarbonyl, 1-ethyl-2-cyclopentenyloxy-carbonylmethyl, 1-ethoxyethoxycarbonylmethyl, 2-tetrahydropyranyloxycarbonylmethyl, and 2-tetrahydrofuranyloxycarbonylmethyl.

The polymer of the invention may be prepared by polymerizing an ester compound of formula (1) or by copolymerizing a first monomer in the form of an ester compound of formula (1) with a second monomer in the form of at least one compound of formulae (2) to (10). By properly adjusting the proportion of the respective monomers used in the copolymerization reaction, the polymer can be tailored so that it may exert the preferred performance when blended in resist compositions.

In addition to (i) the monomer of formula (1) and (ii) the monomer or monomers of formulae (2) to (10), the polymer of the invention may have copolymerized therewith (iii) another monomer having a carbon-to-carbon double bond other than (i) and (ii). Examples of the additional monomer (iii) include substituted acrylic acid esters such as methyl methacrylate, methyl crotonate, dimethyl maleate, and dimethyl itaconate, unsaturated carboxylic acids such as maleic acid, fumaric acid and itaconic acid, substituted or unsubstituted norbornenes such as norbornene and methyl norbornene-5-carboxylate, and unsaturated acid anhydrides such as itaconic anhydride.

The polymers of the invention may contain (I) more than 0 mol % to 100 mol %, preferably 20 to 90 mol %, more preferably 30 to 80 mol % of units of formula (1a-1) or (1a-2) derived from the monomer of formula (1), (II) 0 mol % to less than 100 mol %, preferably 1 to 95 mol %, more preferably 5 to 90 mol % of units of one or more types of formulae (2a) to (10a) derived from the monomers of formulae (2) to (10), and optionally, (III) 0 to 80 mol %, preferably 0 to 70 mol %, more preferably 0 to 50 mol % of units of one or more types derived from the additional monomers (iii).

The polymers of the invention have a weight average molecular weight of 1,000 to 500,000, preferably 3,000 to 100,000. Outside the range, the etching resistance may become extremely low and the resolution may become low because a substantial difference in rate of dissolution before and after exposure is lost.

In the method according to the third aspect of the invention, a polymer is prepared by effecting radical polymerization, anionic polymerization or coordination polymerization between an ester compound of formula (1) and another compound having a carbon-to-carbon double bond, which is typically selected from the above-described monomers (ii) and (iii).

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyl lithium and sec-butyl lithium, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkyl aluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base polymer of a resist composition, the fourth aspect of the invention provides a resist composition comprising the polymer. Specifically, the resist composition is defined as comprising the polymer, a photoacid generator, and an organic solvent.

Photoacid Generator

The photoacid generator is a compound capable of generating an acid upon exposure to high energy radiation or electron beams and includes the following:

(i) onium salts of the formula (P1a-1), (P1a-2) or (P1b), (ii) diazomethane derivatives of the formula (P2), (iii) glyoxime derivatives of the formula (P3), (iv) bissulfone derivatives of the formula (P4), (v) sulfonic acid esters of N-hydroxyimide compounds of the formula (P5), (vi) β-ketosulfonic acid derivatives, (vii) disulfone derivatives, (viii) nitrobenzylsulfonate derivatives, and (ix) sulfonate derivatives.

These photoacid generators are described in detail.
(i) Onium salts of formula (P1a-1), (P1a-2) or (P1b):

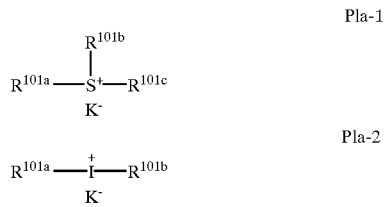

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101}a$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxo-alkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

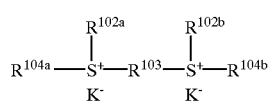

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane derivatives of formula (P2)

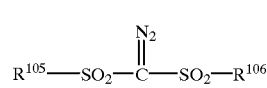

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

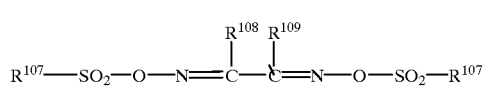

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

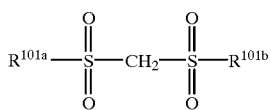

Herein, $R^{101a}$ and $R^{101b}$ are as defined above.

(v) Sulfonic acid esters of N-hydroxyimide compounds of formula (P5)

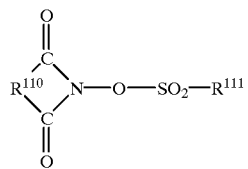

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:
onium salts such as diphenyliodonium trifluoromethanesulfonate, (p-tert-butoxyphenyl) phenyliodonium trifluoromethanesulfonate, diphenyliodonium p-toluenesulfonate, (p-tert-butoxyphenyl) phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl) phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl) diazomethane, bis(p-toluenesulfonyl)diazomethane, bis(xylenesulfonyl)diazomethane, bis (cyclohexylsulfonyl)diazomethane, bis (cyclopentylsulfonyl)diazomethane, bis(n-butylsulfonyl)diazomethane, bis(isobutylsulfonyl) diazomethane, bis(sec-butylsulfonyl)diazomethane, bis (n-propylsulfonyl)diazomethane, bis (isopropylsulfonyl)diazomethane, bis(tert-butylsulfonyl)diazomethane, bis(n-amylsulfonyl) diazomethane, bis(isoamylsulfonyl)diazomethane, bis (sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl) diazomethane, and 1-tert-amylsulfonyl-1-(tert-butylsulfonyl)diazomethane;

glyoxime derivatives such as bis-o-(p-toluenesulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-o-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexanesulfonyl)-α-dimethylglyoxime, bis-o-(benzenesulfonyl)-α-dimethylglyoxime, bis-o-(p- fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, and bis-o-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylulfonylmethane, bisisopropylsulfonylmethane, bis-p-toluenesulfonylmethane, and bisbenzenesulfonylmethane;

β-ketosulfone derivatives such as 2-cyclohexylarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris-(methanesulfonyloxy)benzene, 1,2,3-tris(trifluoromethanesulfonyloxy)benzene, and 1,2,3-tris (p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxy-succinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl) sulfonium trifluoromethanesulfonate, triphenylsulfonium p-toluenesulfonate, (p-tert-butoxyphenyl) diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl) diazomethane, bis(p-toluenesulfonyl)diazomethane, bis(cyclohexylsulfonyl)diazomethane, bis(n-butylsulfonyl) diazomethane, bis(isobutylsulfonyl)diazomethane, bis(sec-butylsulfonyl)diazomethane, bis(n-propylsulfonyl) diazomethane, bis(isopropylsulfonyl)diazomethane, and bis (tert-butylsulfonyl)diazomethane; glyoxime derivatives such as bis-o-(p-toluenesulfonyl)-α-dimethylglyoxime and bis-o-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would lower the rate of alkali dissolution to reduce the resolution of resist compositions and also lower the heat resistance because of the excessive presence of lower molecular weight components.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator serving as one of the resist components is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

To the resist composition of the invention, another polymer other than the polymer of the invention may also be added. The other polymers that can be added to the resist composition are, for example, those polymers comprising units of the following formula (R1) or (R2) and having a weight average molecular weight of about 1,000 to about 500,000, especially about 5,000 to about 100,000 although the other polymers are not limited thereto.

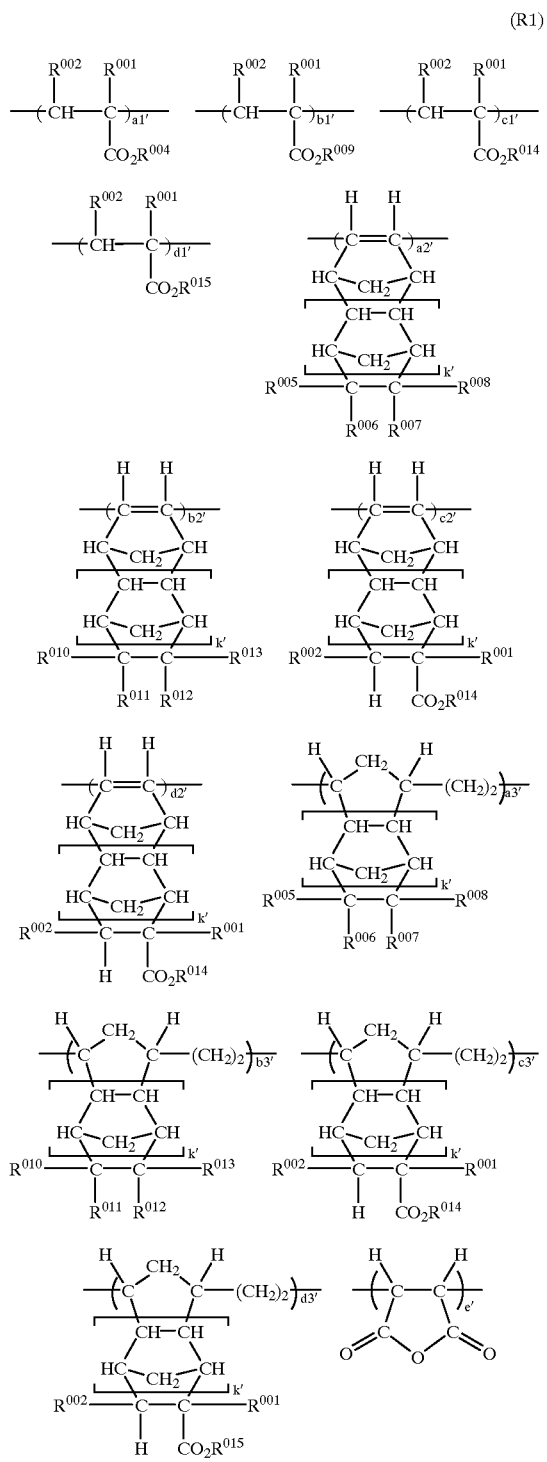

(R1)

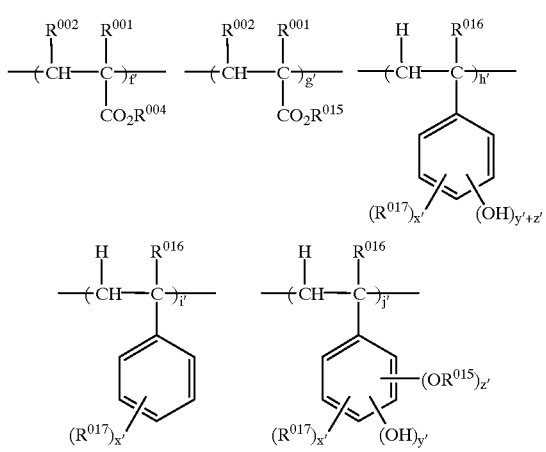

(R2)

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. Letter k' is equal to 0 or 1; a1', a2', a3', b1', b2', b3', c1', c2', c3, d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1 satisfying f'+g'+h'+i'+j'=1. Illustrative examples of the respective groups are the same as exemplified for $R^1$ to $R^{16}$.

The inventive polymer and the other polymer are preferably blended in a weight ratio from 10:90 to 90:10, more preferably from 20:80 to 80:20. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more other polymers may be added. The use of plural polymers allows for easy adjustment of resist properties.

Dissolution Inhibitor

To the resist composition, a dissolution inhibitor may be added. The dissolution inhibitor is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 80 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups or carboxyl groups with acid labile groups is on average at least 0 mol %, and preferably at least 30 mol %, of all the phenolic hydroxyl groups or carboxyl groups. The upper limit is 100 mol %, and preferably 80 mol %.

Preferable examples of such compounds having two or more phenolic hydroxyl groups or compounds having a carboxyl group include those of formulas (D1) to (D14) below.

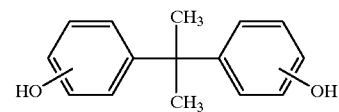

D1

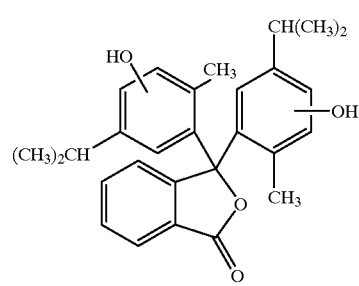

D2

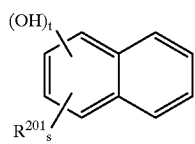

D3

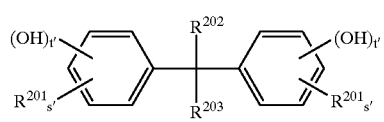

D4

-continued

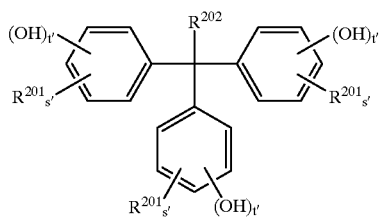

D5

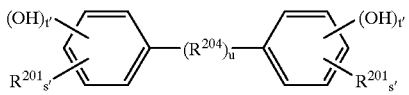

D6

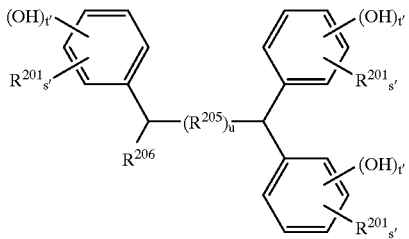

D7

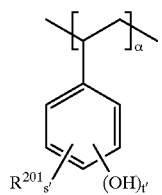

D8

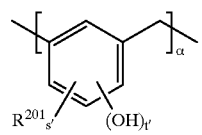

D9

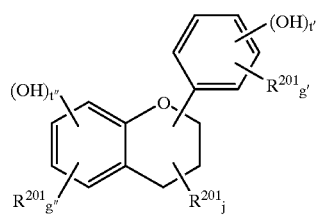

D10

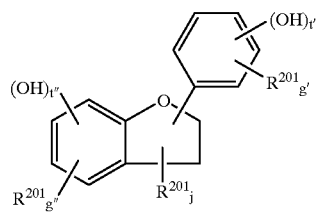

D11

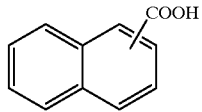

D12

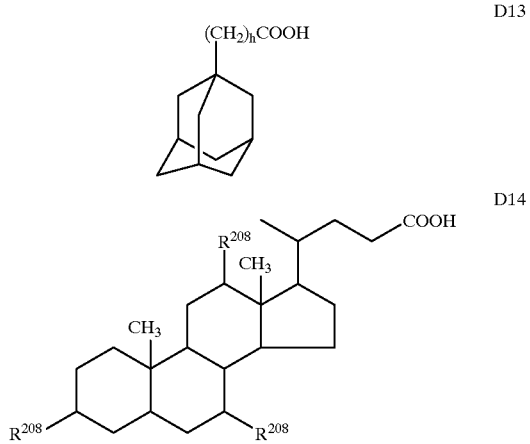

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or —$(R^{207})_h$—COOH; $R^{204}$ is —$(CH_2)_i$— (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and a is a number such that the molecular weight of the compounds of formula (D8) or (D9) is from 20 100 to 1,000.

In the above formulas, suitable examples of $R^{201}$ and $R^{202}$ include hydrogen, methyl, ethyl, butyl, propyl, ethynyl, and cyclohexyl; suitable examples of $R^{203}$ include the same groups as for $R^{201}$ and $R^{202}$, as well as —COOH and —$CH_2$COOH; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, butyl, propyl, ethynyl, cyclohexyl, and hydroxyl-substituted phenyl or naphthyl.

Exemplary acid labile groups on the dissolution inhibitor include groups of the following general formula (11) or (12) above, tertiary alkyl groups of 4 to 20 carbon atoms, trialkylsilyl groups in which each of the alkyls has 1 to 6 carbon atoms, and oxoalkyl groups of 4 to 20 carbon atoms.

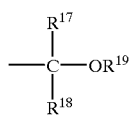 (11)

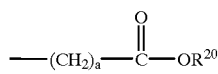 (12)

In these formulas, $R^{17}$ and $R^{18}$ are each hydrogen or a straight, branched or cyclic alkyl having 1 to 18 carbon atoms; and $R^{19}$ is a monovalent hydrocarbon group of 1 to 18 carbon atoms which may contain a heteroatom. $R^{17}$ and $R^{18}$, $R^{17}$ and $R^{19}$, or $R^{18}$ and $R^{19}$ may together form a ring, with the proviso that $R^{17}$, $R^{18}$, and $R^{19}$ are each a straight or branched alkylene of 1 to 18 carbon atoms when they form a ring. Also, $R^{20}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (11). The letter a is an integer from 0 to 6.

The dissolution inhibitor may be formulated in an amount of 0 to 50 parts, preferably 5 to 50 parts, and more preferably 10 to 30 parts, per 100 parts of the base resin, and may be used singly or as a mixture of two or more thereof. Less than 5 parts of the dissolution inhibitor may fail to yield an improved resolution, whereas the use of more than 50 parts would lead to thinning of the patterned film, and thus a decline in resolution.

The dissolution inhibitor can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethyl-aniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazolidine derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (B1) and (B2) may also be included.

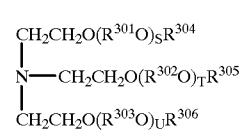

B1

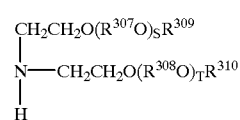

B2

In the formulas, $R^{301}$, $R^{302}$, $R^{303}$, $R^{307}$ and $R^{308}$ are independently straight, branched or cyclic alkylenes of 1 to 20 carbon atoms; $R^{304}$, $R^{305}$, $R^{306}$, $R^{309}$ and $R^{310}$ are hydrogen, alkyls of 1 to 20 carbon atoms, or amino; $R^{304}$ and $R^{305}$, $R^{304}$ and $R^{306}$, $R^{305}$ and $R^{307}$, $R^{304}$ with $R^{305}$ and $R^{306}$, and $R^{309}$ and $R^{310}$ may bond together to form rings; and S, T and U are each integers from 0 to 20, with the proviso that hydrogen is excluded from $R^{304}$, $R^{305}$, $R^{306}$, $R^{309}$ and $R^{310}$ when S, T and U are equal to 0.

The alkylene groups represented by $R^{301}$, $R^{302}$, $R^{303}$, $R^{307}$ and $R^{308}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{304}$, $R^{305}$, $R^{306}$, $R^{309}$ and $R^{310}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{304}$ and $R^{305}$, $R^{304}$ and $R^{306}$, $R^{305}$ and $R^{306}$, $R^{304}$ with $R^{305}$ and $R^{306}$, and $R^{309}$ and $R^{310}$ form rings, the rings preferably have 1 to 20 carbon atoms, more preferably 1 to 8 carbon atoms, and most preferably 1 to 6 carbon atoms, and may have branching alkyl groups of 1 to 6 carbon atoms, and especially 1 to 4 carbon atoms.

S, T, and U are each integers from 0 to 20, preferably from 1 to 10, and more preferably from 1 to 8.

Illustrative examples of the compounds of formulas (B1) and (B2) include tris{2-(methoxymethoxy)ethyl}amine, tris{2-(methoxyethoxy)ethyl}amine, tris[2-{(2-methoxyethoxy)methoxy}ethyl]amine, tris{2-(2-methoxyethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[{(2-hydroxyethoxy)ethoxy}ethyl]amine, 4,7,13,16,21,24-hexaoxa-1,10-diazabicyclo[8.8.8]-hexacosane, 4,7,13,18-tetraoxa-1,10-diazabicyclo[8.5.5]-eicosane, 1,4,10,13-tetraoxa-7,16-diazabicyclooctadecane, 1-aza-12-crown-4, 1-aza-15-crown-5, and 1-aza-18-crown-6. Especially preferred basic compounds are tertiary amines, aniline derivatives, pyrrolidine derivatives, pyridine derivatives, quinoline derivatives, amino acid derivatives, hydroxyl group-bearing nitrogenous compounds, hydroxyphenyl group-bearing nitrogenous compounds, alcoholic nitrogenous compounds, amide derivatives, imide derivatives, tris{2-(methoxymethoxy)ethyl}amine, tris{2-(2-methoxyethoxy)ethyl}amine, tris[2-{(2-methoxyethoxy)ethyl}ethyl]amine, and 1-aza-15-crown-5.

The basic compound is preferably formulated in an amount of 0.001 to 10 parts, and especially 0.01 to 1 part, per part of the photoacid generator. Less than 0.001 part of the basic compound fails to achieve the desired effects thereof, while the use of more than 10 parts would result in too low a sensitivity and resolution.

Other Components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates.

Group I

Compounds in which some or all of the hydrogen atoms on the phenolic hydroxyl groups of the compounds of general formulas (A1) to (A10) below have been replaced with —$R^{401}$—COOH (wherein $R^{401}$ is a straight or branched alkylene of 1 to 10 carbon atoms), and in which the molar ratio C/(C+D) of phenolic hydroxyl groups (C) to ≡C—COOH groups (D) in the molecule is from 0.1 to 1.0.

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a —$(R^{409})_h$—COOR' group (R' being hydrogen or —$R^{409}$—COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$—COOH group;

$R^{411}$ is a straight or branched alkylene of 1 to 10 carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; K is a number such that the compound of formula (A6) may have a weight average molecular weight of 1,000 to 5,000; and λ is a number such that the compound of formula (A7) may have a weight average molecular weight of 1,000 to 10,000.

Group II

Compounds of general formulas (A11) to (A15) below.

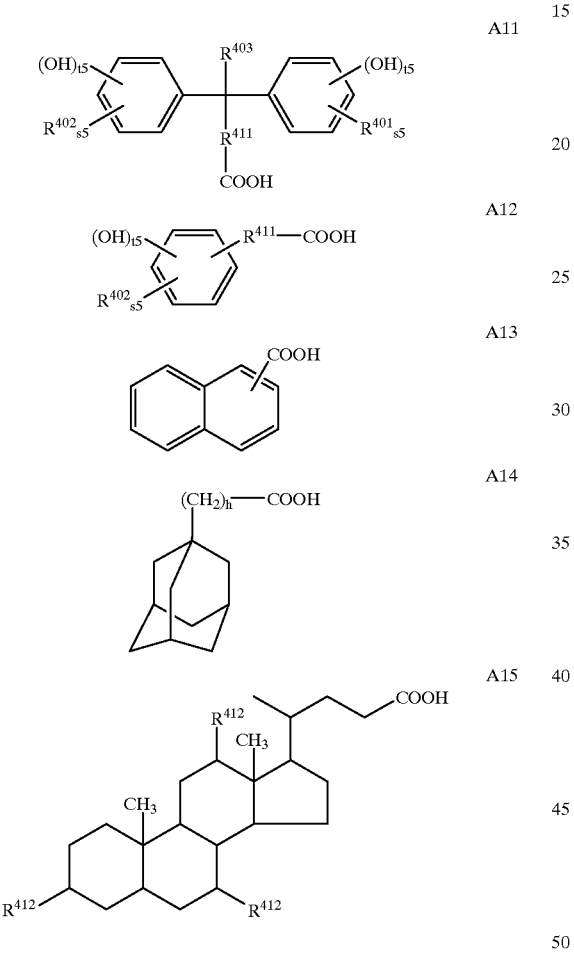

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

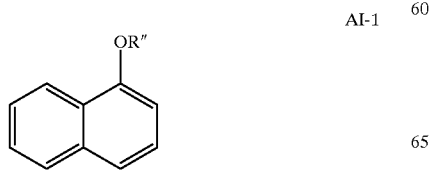

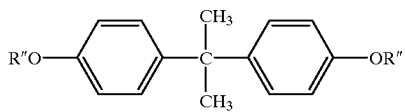

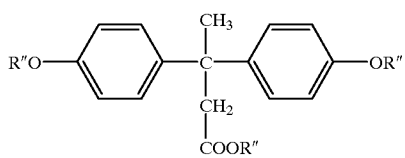

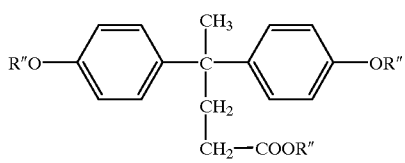

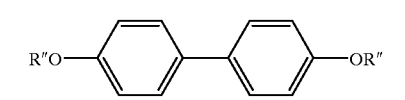

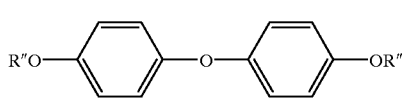

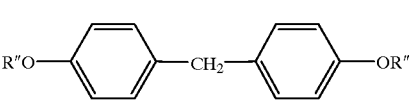

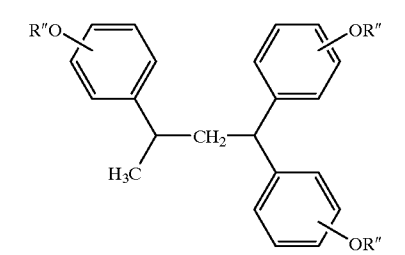

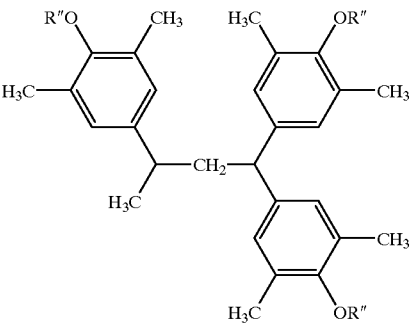

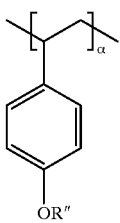

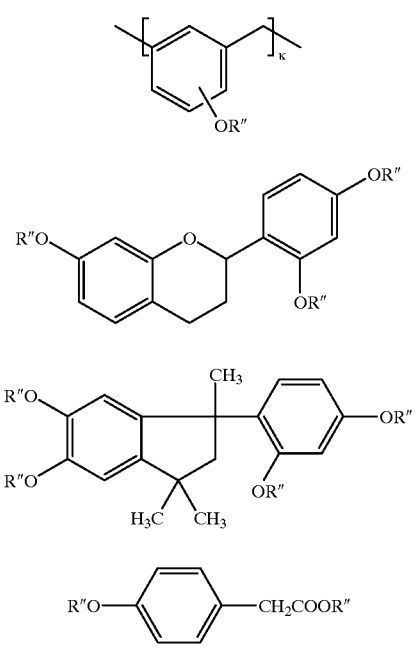

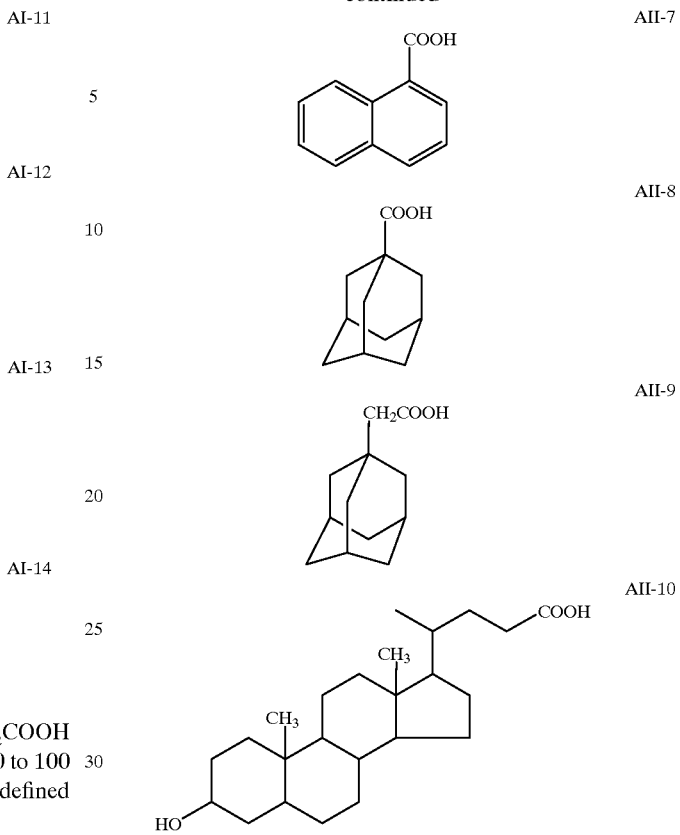

In the above formulas, R" is hydrogen or a CH$_2$COOH group such that the CH$_2$COOH group accounts for 10 to 100 mol % of R" in each compound, α and κ are as defined above.

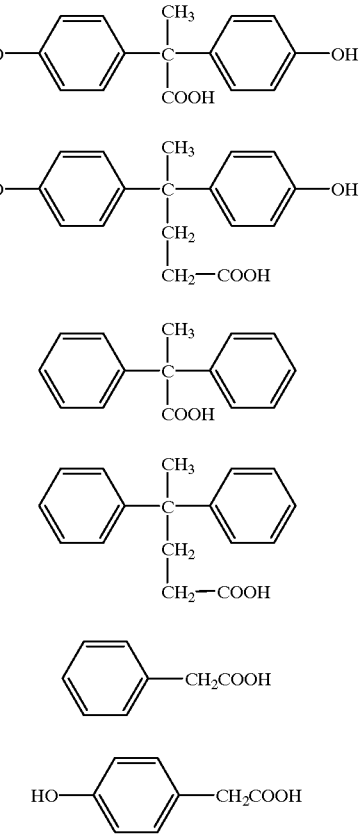

The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (S1) or (S2) below.

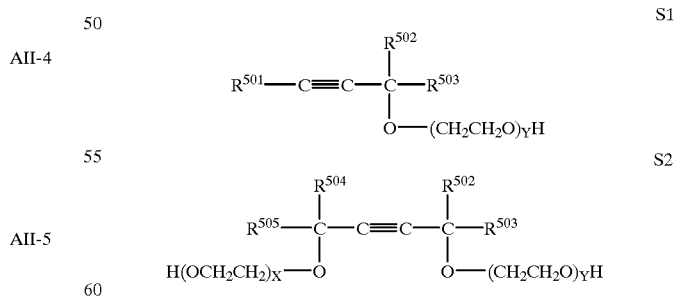

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include, as an optional ingredient, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M K.K., Surflon S-141 and S-145 from Asahi Glass K.K., Unidine DS-401, DS-403 and DS-451 from Daikin Industry K.K., Megafac F-8151 from Dai-Nippon Ink & Chemicals K.K., and X-70-092 and X-70-093 from Shin-Etsu Chemical Co., Ltd. Preferred surfactants are Florade FC-430 from Sumitomo 3M K.K. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.5 to 2.0 μm, which is then pre-baked on a hot plate at 60 to 150° C. for 1 to 10 minutes, and preferably at 80 to 120° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 1 to 5 minutes, and preferably at 80 to 120° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 193 to 248 nm, an excimer laser, x-rays, or an electron beam. The desired pattern may not be obtainable outside the upper and lower limits of the above range.

The resist composition comprising the polymer of the invention as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed.

EXAMPLE

Examples of the invention are given below by way of illustration and not by way of limitation.

First described are examples of synthesizing ester compounds according to the invention and examples of preparing polymers therefrom.

Synthetic Example 1-1

Synthesis of Monomer 1

In 3 liters of tetrahydrofuran was dissolved 778.6 g of ethyl bromide. Below 60° C., this reaction mixture was added dropwise to 171.4 g of metallic magnesium over one hour. After agitation was continued for 2 hours at room temperature, 300.0 g of cyclopentanone was added dropwise over 45 minutes to the reaction mixture which was kept below 65° C. After agitation was continued for one hour at room temperature, the reaction solution was worked up in a conventional manner. The resulting oily substance was distilled in vacuum, collecting 209.2 g of 1-ethylcyclopentanol. The yield was 51.4%.

In 2 liters of methylene chloride was dissolved 197.0 g of 1-ethylcyclopentanol. To this reaction mixture kept below −20° C., 204.0 g of acrylic acid chloride was added dropwise over 10 minutes. To the reaction mixture, 2.1 g of 4-(N,N-dimethylamino)pyridine was added, and 263.0 g of triethylamine was added dropwise over one hour while maintaining below −20° C. After agitation was continued for 15 hours at room temperature, the reaction solution was worked up in a conventional manner. There was obtained about 300 g of an oily substance. This was used in the subsequent reaction without purification.

The oily substance obtained in the above step was dissolved in 300 ml of benzene. To this reaction mixture kept below 10° C., 172.0 g of cyclopentadiene was added dropwise over 10 minutes. Agitation was continued for 17 hours at room temperature, then for one hour at 70° C. The reaction solution was concentrated in vacuum. The resulting oily substance was distilled in vacuum, collecting 269.9 g of 5-norbornene-2-carboxylic acid 1-ethylcyclopentyl, designated Monomer 1. The yield was 66.7%.

Boiling point: 108–116° C./1 mmHg $^1$H-NMR (CDCl$_3$, 270 MHz): δ 0.78–0.90 (m, 3H), 1.20–2.18 (m, 14H), 2.83–3.20 (m, 3H), 5.89–6.20 (m, 2H)

FT-IR: 1726 cm$^{-1}$

Synthetic Examples 1-2 to 1-16

Synthesis of Monomers 2 to 16

Monomers 2 to 16 were synthesized by the same procedure as Synthetic Example 1—1.

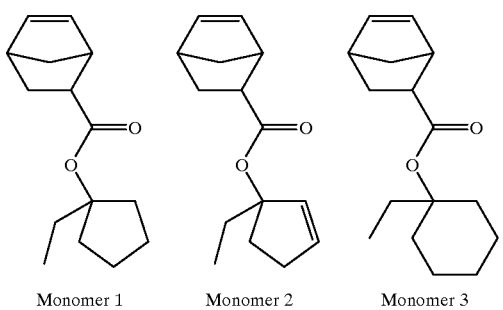

Monomer 1    Monomer 2    Monomer 3

-continued

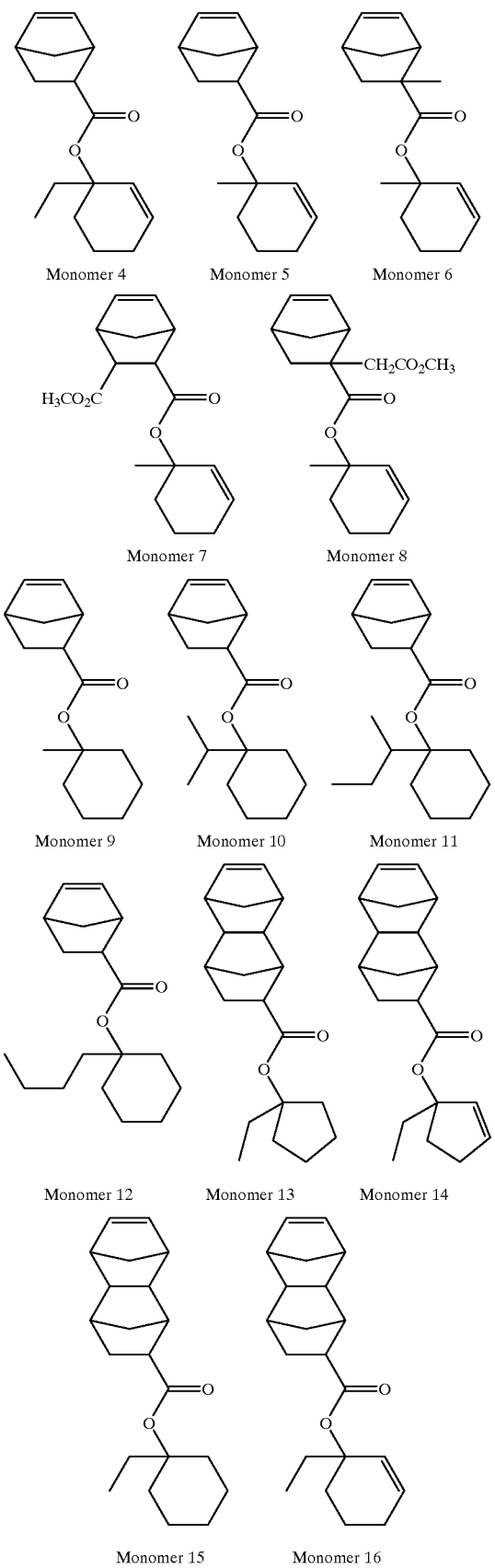

Monomer 4 Monomer 5 Monomer 6

Monomer 7 Monomer 8

Monomer 9 Monomer 10 Monomer 11

Monomer 12 Monomer 13 Monomer 14

Monomer 15 Monomer 16

Synthetic Example 2-1

Synthesis of Polymer 1

In 2 liters of tetrahydrofuran, 117.0 g of Monomer 1 and 49.0 g of maleic anhydride were dissolved, and 3.5 g of 2,2'-azobisisobutyronitrile added. After agitation was continued for 15 hours at 60° C., the reaction solution was concentrated in vacuum. The residue was dissolved in 800 ml of tetrahydrofuran and added dropwise to 20 liters of n-hexane. The resulting solids were collected by filtration, washed with 20 liters of n-hexane, and dried in vacuum at 40° C. for 6 hours, obtaining 88.3 g of a polymer, designated Polymer 1. The yield was 53.2%.

Synthetic Examples 2-2 to 2-48

Synthesis of Polymers 2 to 48

Polymers 2 to 48 were synthesized by the same procedure as Synthetic Example 2-1.

(Polymer 1)

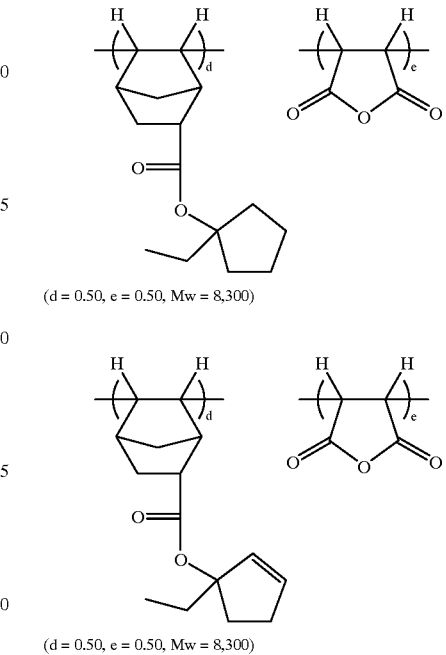

($d = 0.50$, $e = 0.50$, $Mw = 8,300$)

(Polymer 2)

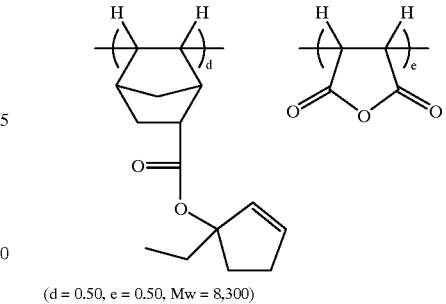

($d = 0.50$, $e = 0.50$, $Mw = 8,300$)

(Polymer 3)

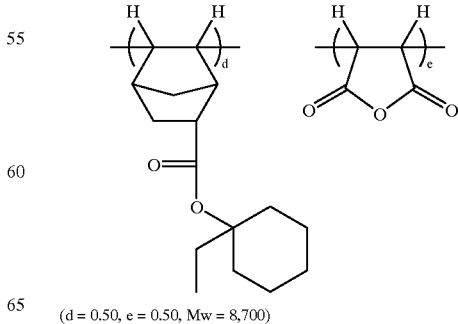

($d = 0.50$, $e = 0.50$, $Mw = 8,700$)

(Polymer 4)
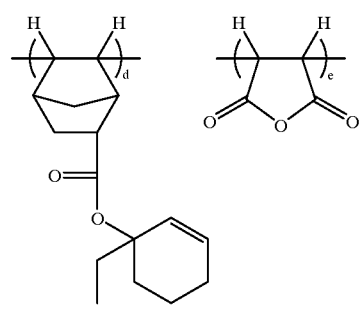
(d = 0.50, e = 0.50, Mw = 8,600)
(Polymer 5)
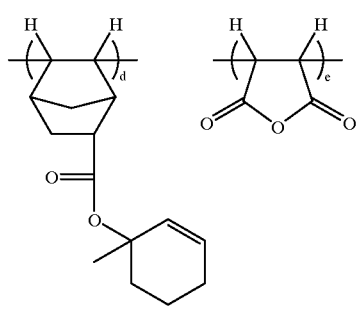
(d = 0.50, e = 0.50, Mw = 8,300)
(Polymer 6)
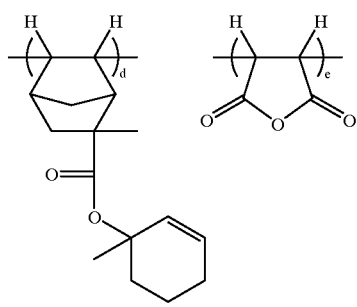
(d = 0.50, e = 0.50, Mw = 8,600)
(Polymer 7)
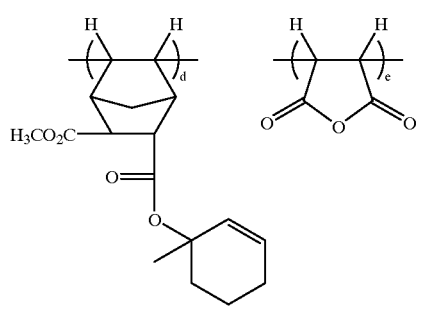
(d = 0.50, e = 0.50, Mw = 9,700)
(Polymer 8)
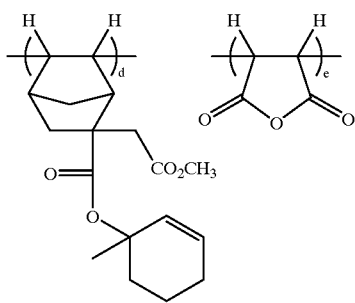
(d = 0.50, e = 0.50, Mw = 10,100)
(Polymer 9)
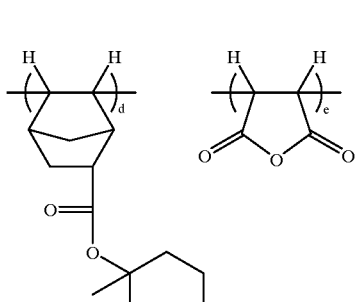
(d = 0.50, e = 0.50, Mw = 8,300)
(Polymer 10)
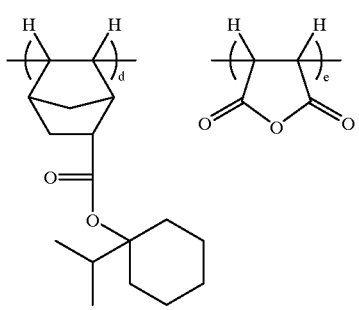
(d = 0.50, e = 0.50, Mw = 9,000)
(Polymer 11)
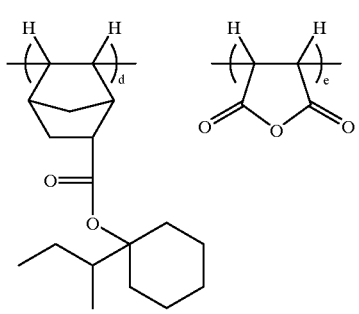
(d = 0.50, e = 0.50, Mw = 9,400)

(Polymer 12)
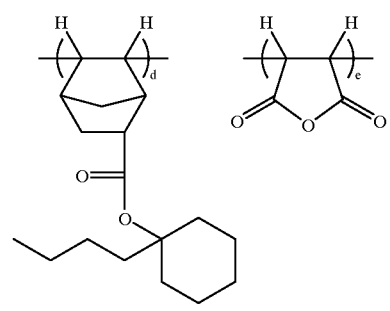
(d = 0.50, e = 0.50, Mw = 9,400)
(Polymer 13)
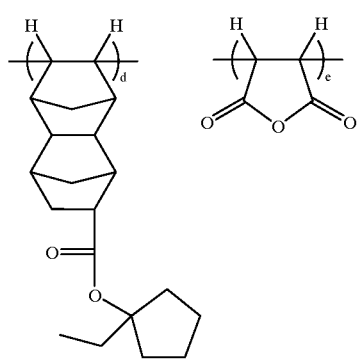
(d = 0.50, e = 0.50, Mw = 10,000)
(Polymer 14)
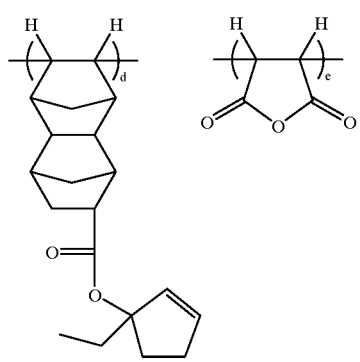
(d = 0.50, e = 0.50, Mw = 9,900)
(Polymer 15)
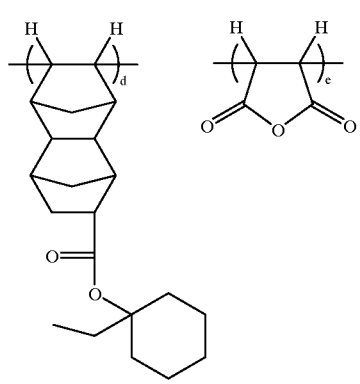
(d = 0.50, e = 0.50, Mw = 10,300)
(Polymer 16)
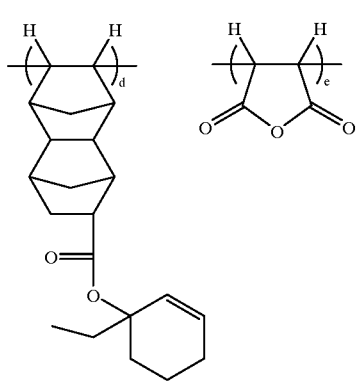
(d = 0.50, e = 0.50, Mw = 10,300)
(Polymer 17)
(a2 = 0.10, b2 = 0.30, d = 0.60, Mw = 20,800)
(Polymer 18)
(a2 = 0.10, b2 = 0.30, d = 0.60, Mw = 21,400)
(Polymer 19)
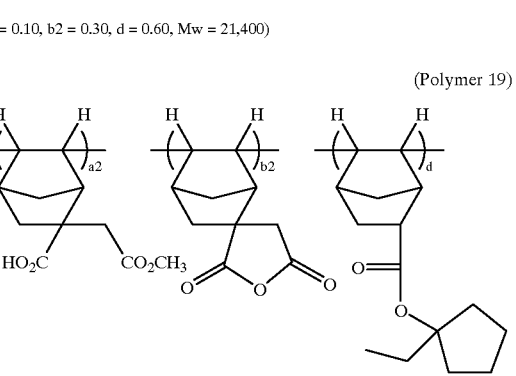
(a2 = 0.10, b2 = 0.30, d = 0.60, Mw = 21,500)

(Polymer 20)
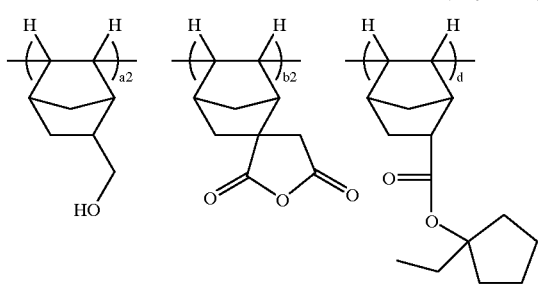
(a2 = 0.10, b2 = 0.30, d = 0.60, Mw = 21,600)
(Polymer 21)
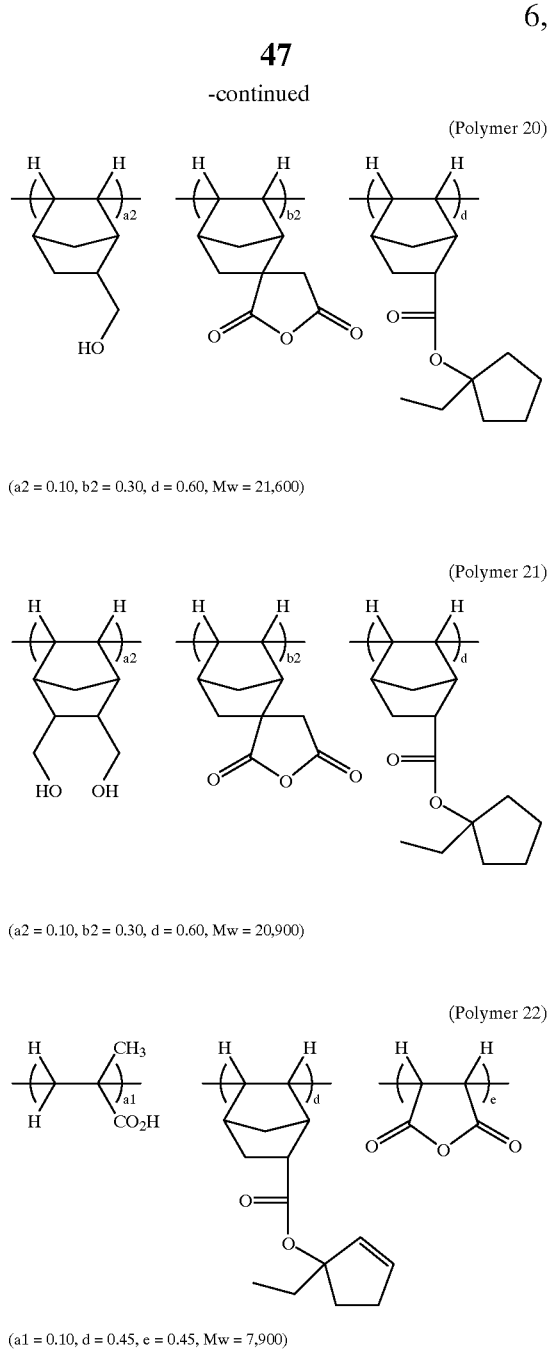
(a2 = 0.10, b2 = 0.30, d = 0.60, Mw = 20,900)
(Polymer 22)
(a1 = 0.10, d = 0.45, e = 0.45, Mw = 7,900)
(Polymer 23)
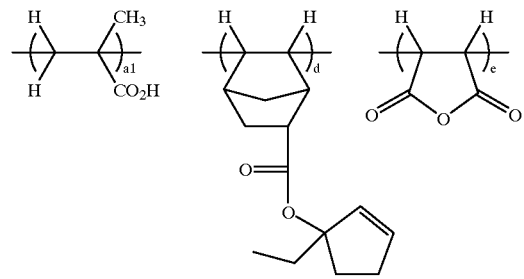
(a1 = 0.10, d = 0.45, e = 0.45, Mw = 8,300)
(Polymer 24)
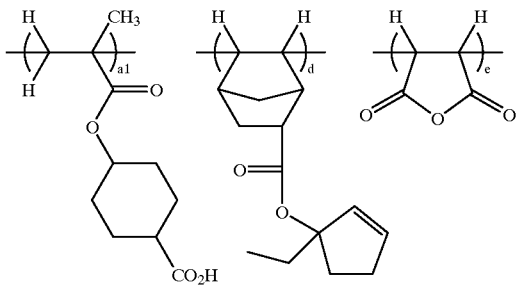
(a1 = 0.10, d = 0.45, e = 0.45, Mw = 8,500)
(Polymer 25)
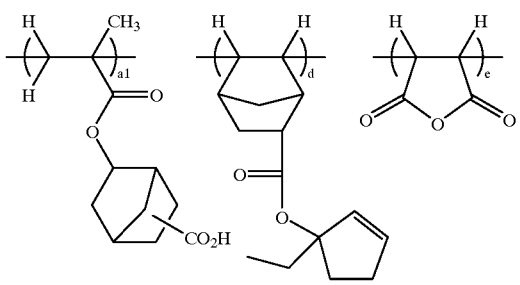
(a1 = 0.10, d = 0.45, e = 0.45, Mw = 8,600)
(Polymer 26)
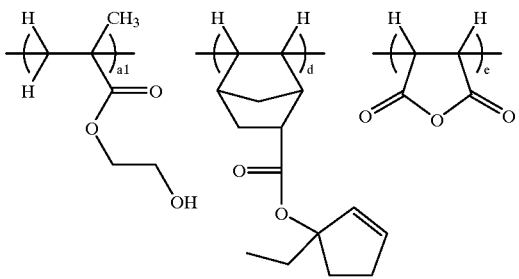
(a1 = 0.10, d = 0.45, e = 0.45, Mw = 8,100)
(Polymer 27)
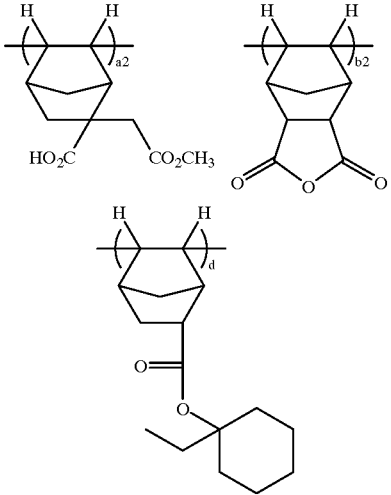
(a2 = 0.15, b2 = 0.20, d = 0.65, Mw = 33,900)

(Polymer 28)
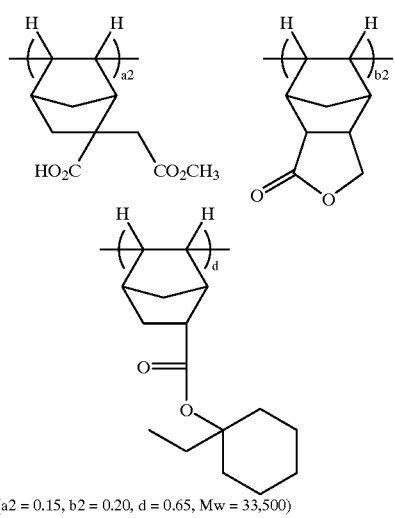
(a2 = 0.15, b2 = 0.20, d = 0.65, Mw = 33,500)
(Polymer 29)
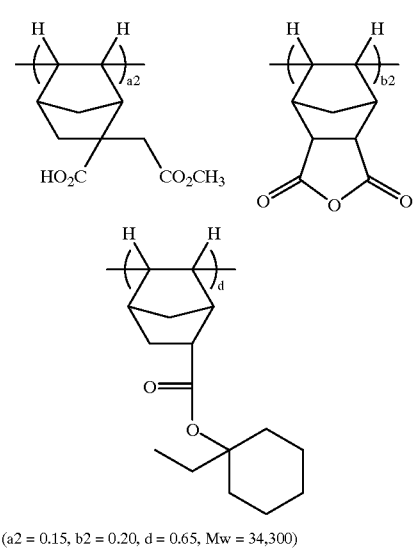
(a2 = 0.15, b2 = 0.20, d = 0.65, Mw = 34,300)
(Polymer 30)
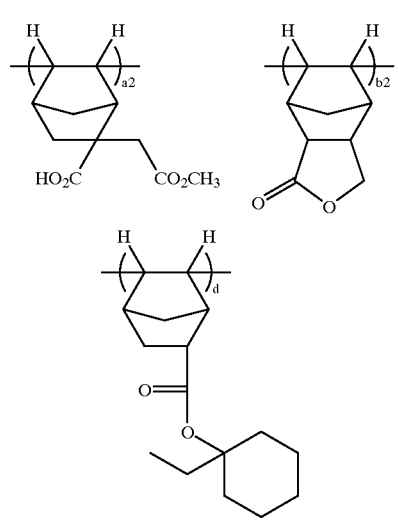
(a2 = 0.15, b2 = 0.20, d = 0.65, Mw = 33,900)
(Polymer 31)
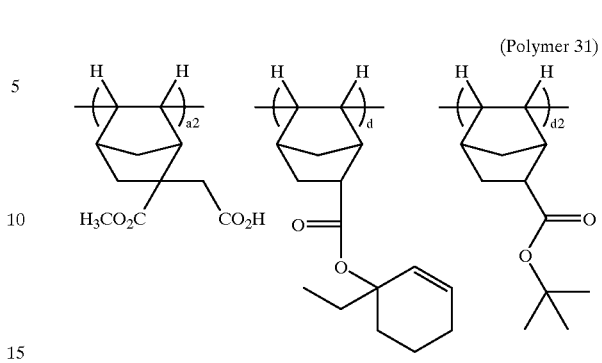
(a2 = 0.30, d = 0.40, d2 = 0.30, Mw = 32,400)
(Polymer 32)
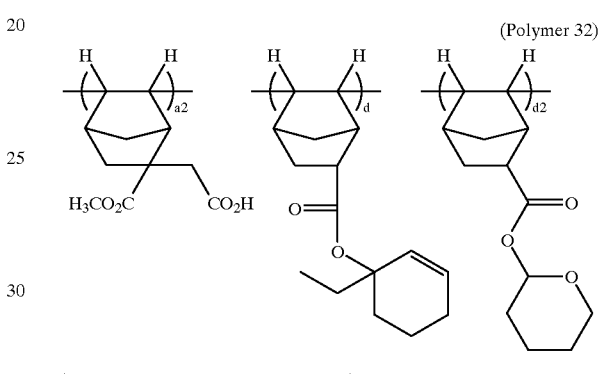
(a2 = 0.30, d = 0.40, d2 = 0.30, Mw = 33,600)
(Polymer 33)
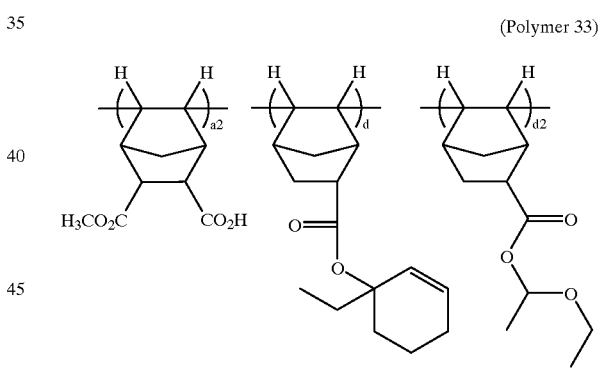
(a2 = 0.30, d = 0.40, d2 = 0.30, Mw = 33,100)
(Polymer 34)
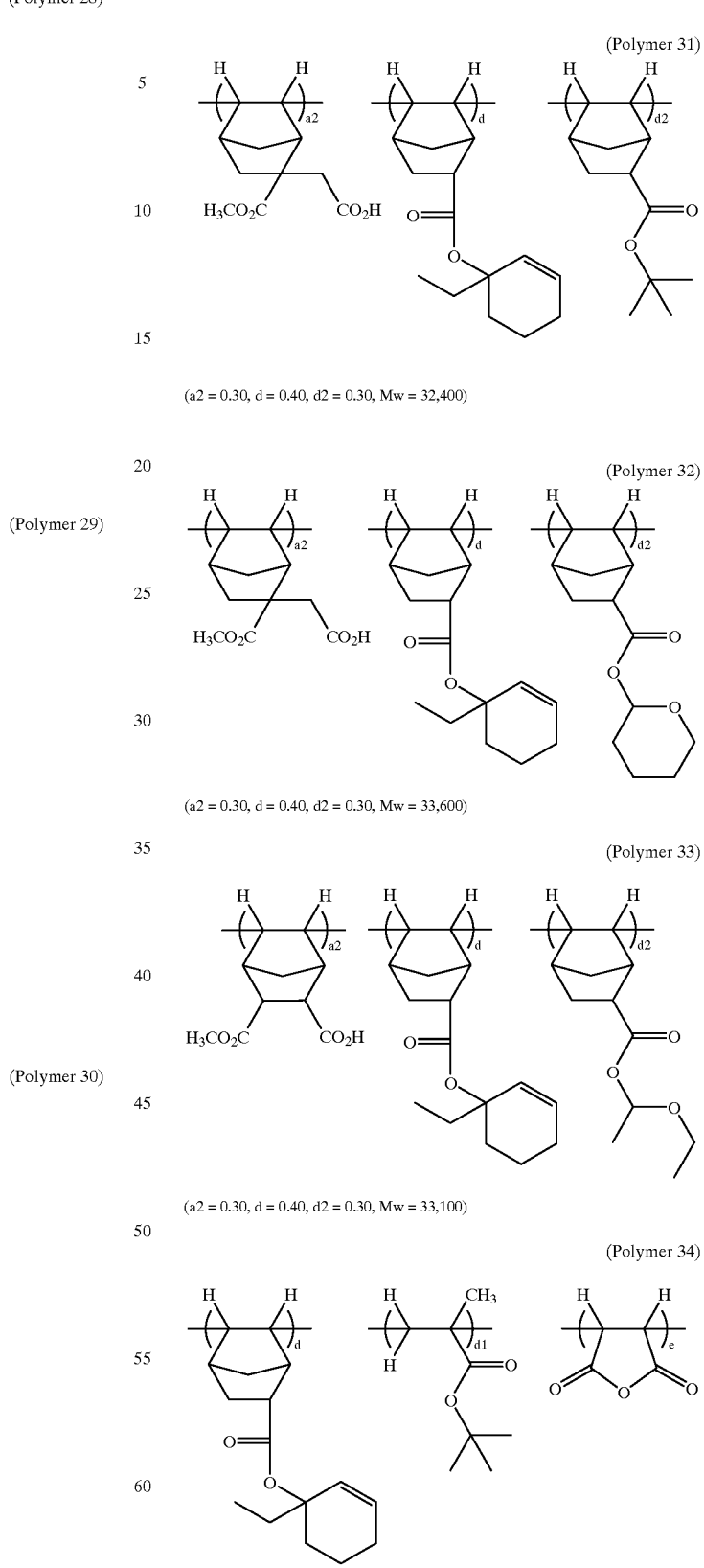
(d = 0.35, d1 = 0.30, e = 0.35, Mw = 8,200)

(Polymer 35)
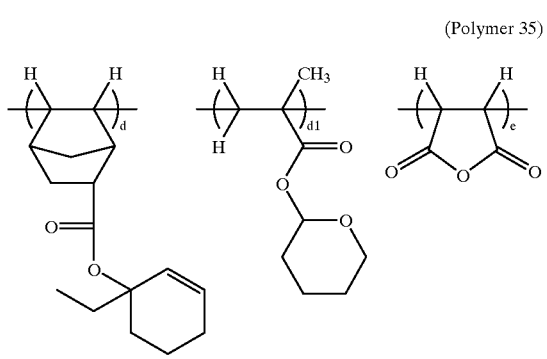
(d = 0.35, d1 = 0.30, e = 0.35, Mw = 8,600)
(Polymer 36)
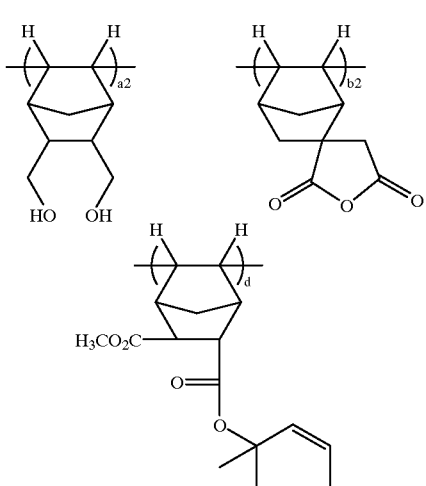
(d = 0.35, d1 = 0.30, e = 0.35, Mw = 8,400)
(Polymer 37)
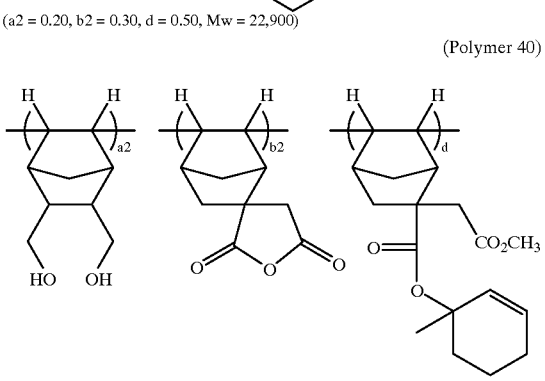
(a2 = 0.20, b2 = 0.30, d = 0.50, Mw = 20,000)
(Polymer 38)
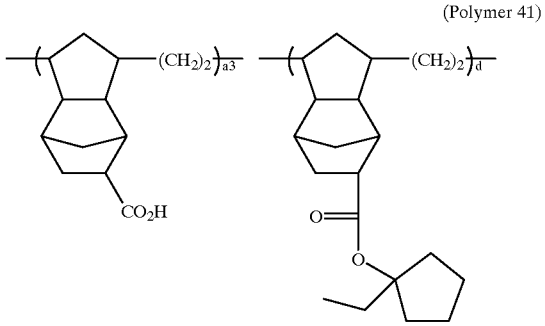
(a2 = 0.20, b2 = 0.30, d = 0.50, Mw = 20,700)
(Polymer 39)
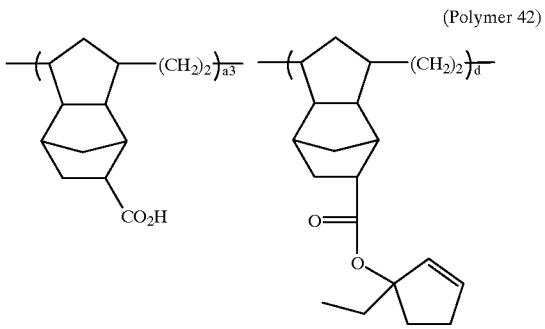
(a2 = 0.20, b2 = 0.30, d = 0.50, Mw = 22,900)
(Polymer 40)
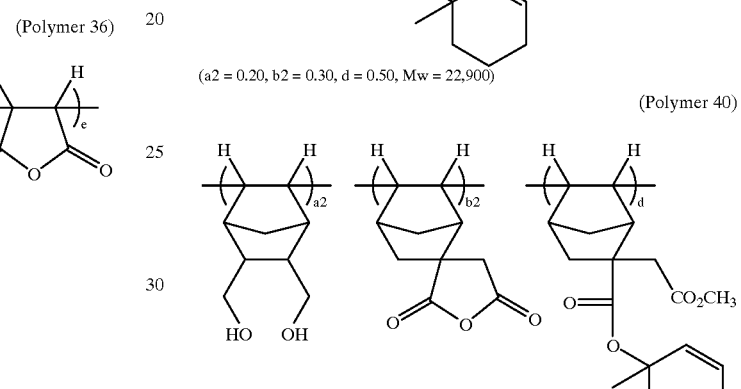
(a2 = 0.20, b2 = 0.30, d = 0.50, Mw = 23,600)
(Polymer 41)
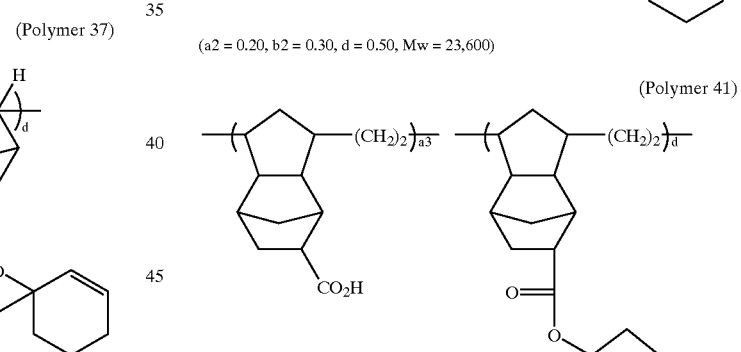
(a3 = 0.20, d = 0.80, Mw = 56,600)
(Polymer 42)
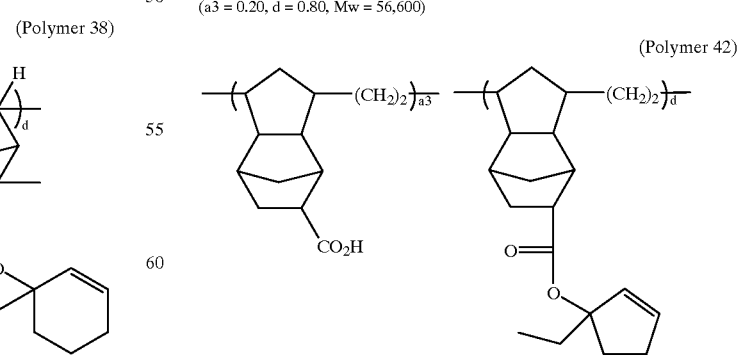
(a3 = 0.20, d = 0.80, Mw = 56,300)

(Polymer 43)

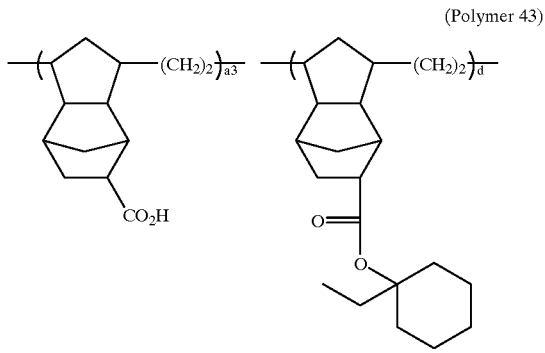

(a3 = 0.20, d = 0.80, Mw = 58,900)

(Polymer 44)

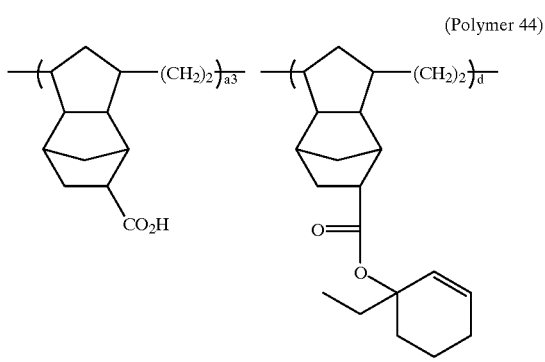

(a3 = 0.20, d = 0.80, Mw = 58,600)

(Polymer 45)

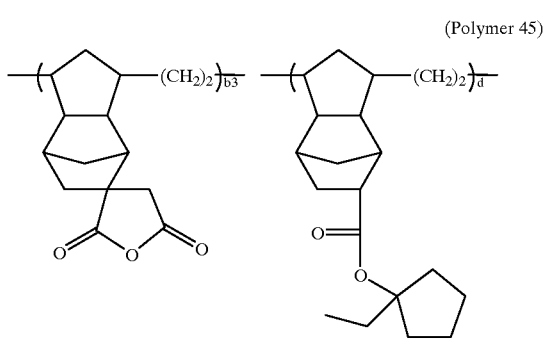

(b3 = 0.30, d = 0.70, Mw = 57,100)

(Polymer 46)

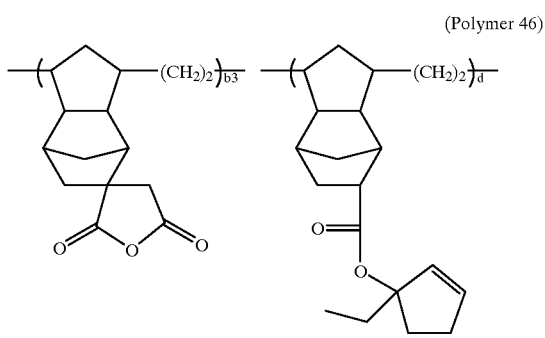

(b3 = 0.30, d = 0.70, Mw = 56,800)

(Polymer 47)

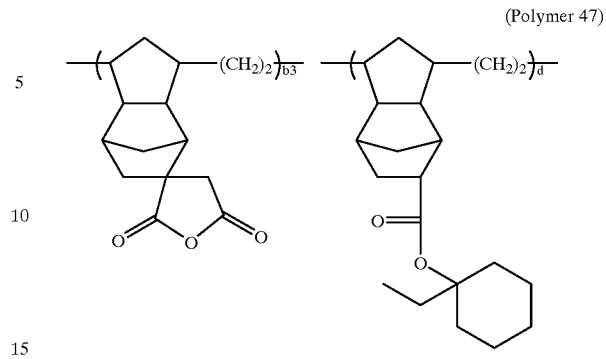

(b3 = 0.30, d = 0.70, Mw = 59,100)

(Polymer 48)

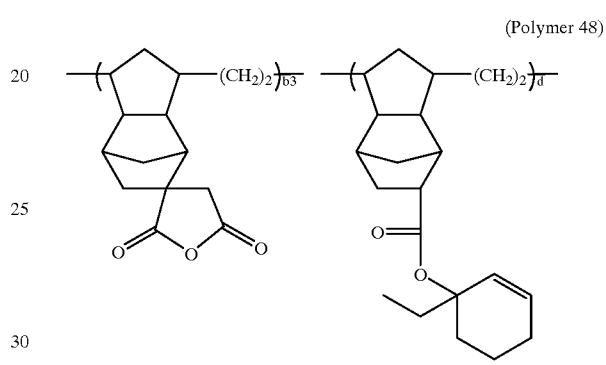

(b3 = 0.30, d = 0.70, Mw = 58,800)

Example I

Resist compositions were formulated using Polymers 1 to 48 obtained in the above Synthetic Examples and examined for resolution.

Examples I-1 to I-82: Evaluation of resist resolution

Resist compositions were prepared by using Polymers 1 to 48 or Polymers 49 to 56 shown below, and dissolving the polymer, a photoacid generator (designated as PAG 1 to 8), a dissolution inhibitor (designated as DRR 1 to 4), a basic compound, and a compound having a ≡C—COOH group in the molecule (ACC 1) in a solvent containing 0.05% by weight of surfactant Florade FC-430 (Sumitomo 3M) in the combination shown in Table 1. These compositions were each filtered through a 0.2 μm Teflon filter, thereby giving resist solutions.

(Polymer 49)
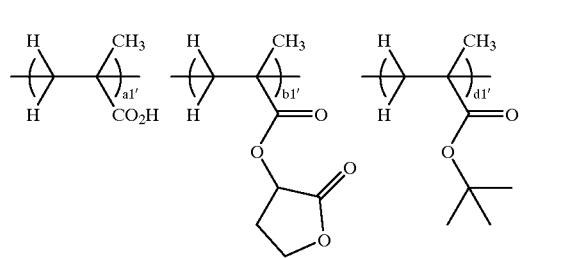
(a1' = 0.10, b1' = 0.20, d1' = 0.70, Mw = 7,100)
(Polymer 50)
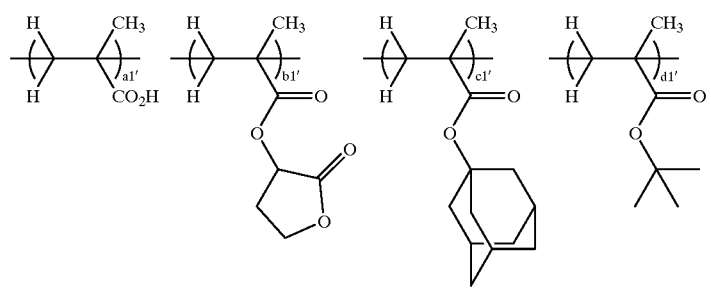
(a1' = 0.10, b1' = 0.20, c1' = 0.20, d1' = 0.50, Mw = 7,900)
(Polymer 51)
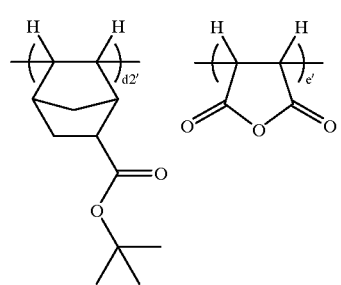
(d2' = 0.50, e' = 0.50, Mw = 7,300)
(Polymer 52)
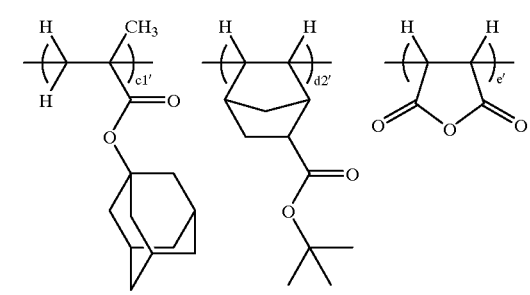
(c1' = 0.20, d2' = 0.40, e' = 0.40, Mw = 8,600)
(Polymer 53)
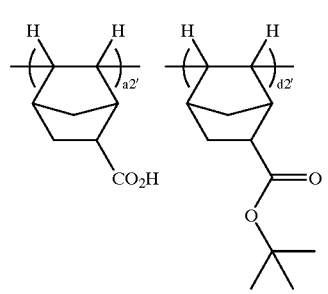
(a2' = 0.20, d2' = 0.80, Mw = 27,500)

(Polymer 54)
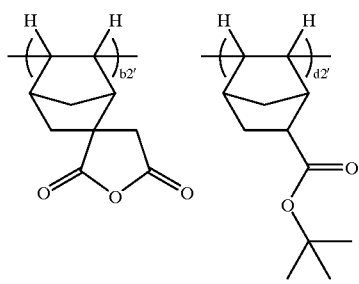
(b2' = 0.30, d2' = 0.70, Mw = 28,400)
(Polymer 55)
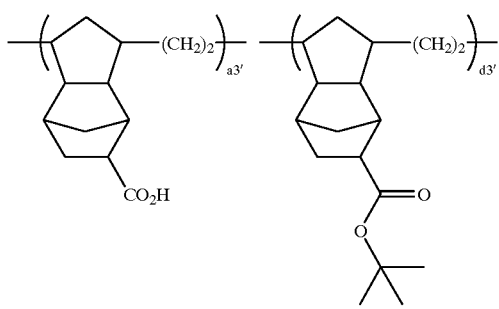
(a3' = 0.20, d3' = 0.80, Mw = 50,200)
(Polymer 56)
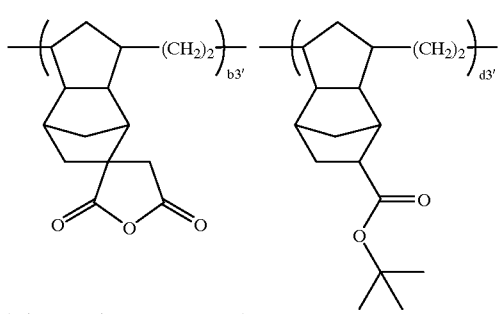
(b3' = 0.30, d3' = 0.70, Mw = 51,500)
(PAG 1)
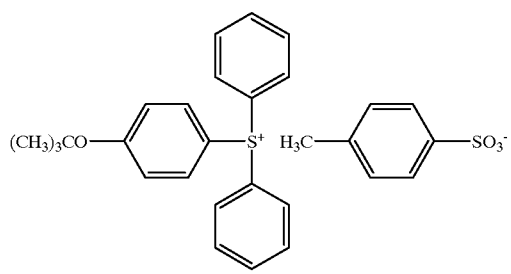
(PAG 2)
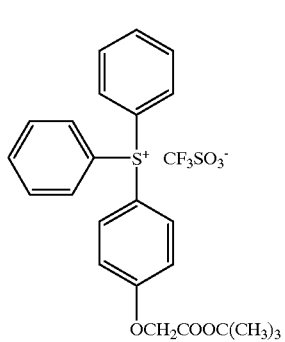

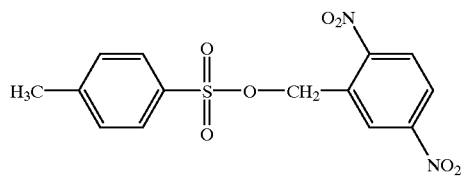
(PAG 3)
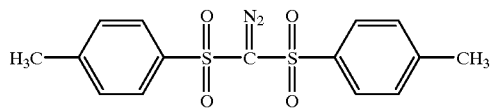
(PAG 4)
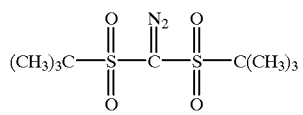
(PAG 5)
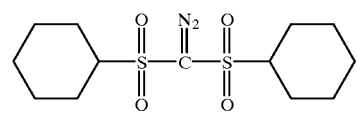
(PAG 6)
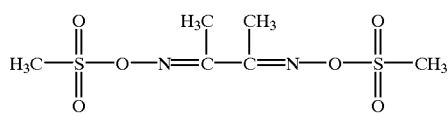
(PAG 7)
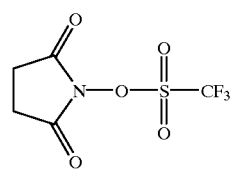
(PAG 8)
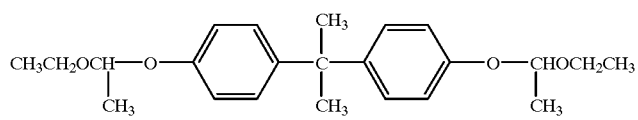
(DRR 1)
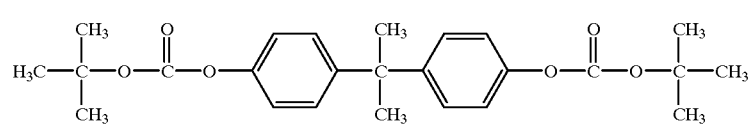
(DRR 2)
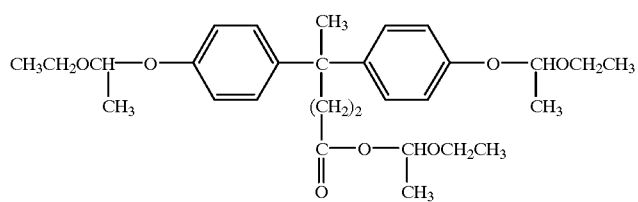
(DRR 3)

-continued

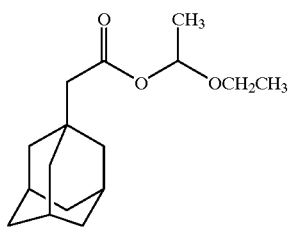

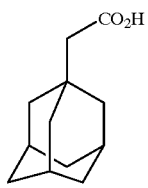

(DRR 4)

(ACC 1)

The solvents and basic compounds used are as follows.
PGMEA: propylene glycol methyl ether acetate
PG/EL: a mixture of 70% PGMEA and 30% ethyl lactate
TBA: tributylamine
TEA: triethanolamine
TMMEA: trismethoxymethoxyethylamine
TMEMEA: trismethoxyethoxymethoxyethylamine These resist solutions were spin-coated onto silicon wafers, then baked at 110° C. for 90 seconds on a hot plate to give resist films having a thickness of 0.5 μm. The resist films were exposed using an ArF excimer laser stepper (Nikon Corporation; NA 0.55), then baked (PED) at 110° C. for 90 seconds, and developed with a solution of 2.38% tetramethylammonium hydroxide in water, thereby giving positive patterns.

The resulting resist patterns were evaluated as described below.

First, the sensitivity (Eth, mJ/cm$^2$) was determined. Next, the optimal dose (sensitivity Eop, mJ/cm$^2$) was defined as the dose which provides a 1:1 resolution at the top and bottom of a 0.25 μm line-and-space pattern, and the resolution of the resist under evaluation was defined as the minimum line width (μm) of the lines and spaces that separated at this dose. The shape of the resolved resist pattern was examined under a scanning electron microscope.

The composition and test results of the resist materials are shown in Table 1.

TABLE 1

| Example | Base resin | Photoacid generator | Dissolution inhibitor | Basic compound | Solvent | Sensitivity | Resolution | Shape |
|---|---|---|---|---|---|---|---|---|
| I-1 | Polymer 1 (80) | PAG 1 (2) | | TBA (0.125) | PGMEA (600) | 6.5 | 0.18 | rectangular |
| I-2 | Polymer 2 (80) | PAG 1 (2) | | TBA (0.125) | PGMEA (600) | 6.0 | 0.18 | rectangular |
| I-3 | Polymer 3 (80) | PAG 1 (2) | | TBA (0.125) | PGMEA (600) | 6.8 | 0.20 | rectangular |
| I-4 | Polymer 4 (80) | PAG 1 (2) | | TBA (0.125) | PGMEA (600) | 6.2 | 0.18 | rectangular |
| I-5 | Polymer 5 (80) | PAG 1 (2) | | TBA (0.125) | PGMEA (600) | 6.3 | 0.18 | rectangular |
| I-6 | Polymer 6 (80) | PAG 1 (2) | | TBA (0.125) | PGMEA (600) | 6.4 | 0.18 | rectangular |
| I-7 | Polymer 7 (80) | PAG 1 (2) | | TBA (0.125) | PGMEA (600) | 6.3 | 0.20 | rectangular |
| I-8 | Polymer 8 (80) | PAG 1 (2) | | TBA (0.125) | PGMEA (600) | 6.3 | 0.20 | rectangular |
| I-9 | Polymer 9 (80) | PAG 1 (2) | | TBA (0.125) | PGMEA (600) | 7.0 | 0.20 | rectangular |
| I-10 | Polymer 10 (80) | PAG 1 (2) | | TBA (0.125) | PGMEA (600) | 6.5 | 0.18 | rectangular |
| I-11 | Polymer 11 (80) | PAG 1 (2) | | TBA (0.125) | PGMEA (600) | 6.6 | 0.18 | rectangular |
| I-12 | Polymer 12 (80) | PAG 1 (2) | | TBA (0.125) | PGMEA (600) | 6.9 | 0.20 | rectangular |
| I-13 | Polymer 13 (80) | PAG 1 (2) | | TBA (0.125) | PGMEA (600) | 6.6 | 0.18 | rectangular |
| I-14 | Polymer 14 (80) | PAG 1 (2) | | TBA (0.125) | PGMEA (600) | 6.2 | 0.18 | rectangular |
| I-15 | Polymer 15 (80) | PAG 1 (2) | | TBA (0.125) | PGMEA (600) | 6.9 | 0.20 | rectangular |

TABLE 1-continued

| Example | Base resin | Photoacid generator | Dissolution inhibitor | Basic compound | Solvent | Sensitivity | Resolution | Shape |
|---|---|---|---|---|---|---|---|---|
| I-16 | Polymer 16 (80) | PAG 1 (2) | | TBA (0.125) | PGMEA (600) | 6.3 | 0.18 | rectangular |
| I-17 | Polymer 17 (80) | PAG 1 (2) | | TBA (0.125) | PGMEA (600) | 6.3 | 0.18 | rectangular |
| I-18 | Polymer 18 (80) | PAG 1 (2) | | TBA (0.125) | PGMEA (600) | 6.2 | 0.18 | rectangular |
| I-19 | Polymer 19 (80) | PAG 1 (2) | | TBA (0.125) | PGMEA (600) | 6.2 | 0.15 | rectangular |
| I-20 | Polymer 20 (80) | PAG 1 (2) | | TBA (0.125) | PGMEA (600) | 6.6 | 0.20 | rectangular |
| I-21 | Polymer 21 (80) | PAG 1 (2) | | TBA (0.125) | PGMEA (600) | 6.5 | 0.18 | rectangular |
| I-22 | Polymer 22 (80) | PAG 1 (2) | | TBA (0.125) | PGMEA (600) | 5.9 | 0.18 | rectangular |
| I-23 | Polymer 23 (80) | PAG 1 (2) | | TBA (0.125) | PGMEA (600) | 6.0 | 0.18 | rectangular |
| I-24 | Polymer 24 (80) | PAG 1 (2) | | TBA (0.125) | PGMEA (600) | 6.0 | 0.18 | rectangular |
| I-25 | Polymer 25 (80) | PAG 1 (2) | | TBA (0.125) | PGMEA (600) | 6.1 | 0.18 | rectangular |
| I-26 | Polymer 26 (80) | PAG 1 (2) | | TBA (0.125) | PGMEA (600) | 6.2 | 0.20 | rectangular |
| I-27 | Polymer 27 (80) | PAG 1 (2) | | TBA (0.125) | PGMEA (600) | 6.7 | 0.18 | rectangular |
| I-28 | Polymer 28 (80) | PAG 1 (2) | | TBA (0.125) | PGMEA (600) | 6.8 | 0.18 | rectangular |
| I-29 | Polymer 29 (80) | PAG 1 (2) | | TBA (0.125) | PGMEA (600) | 6.7 | 0.18 | rectangular |
| I-30 | Polymer 30 (80) | PAG 1 (2) | | TBA (0.125) | PGMEA (600) | 6.8 | 0.18 | rectangular |
| I-31 | Polymer 31 (80) | PAG 1 (2) | | TBA (0.125) | PGMEA (600) | 6.4 | 0.20 | rectangular |
| I-32 | Polymer 32 (80) | PAG 1 (2) | | TBA (0.125) | PGMEA (600) | 6.0 | 0.18 | rectangular |
| I-33 | Polymer 33 (80) | PAG 1 (2) | | TBA (0.125) | PGMEA (600) | 5.9 | 0.18 | retangular |
| I-34 | Polymer 34 (80) | PAG 1 (2) | | TBA (0.125) | PGMEA (600) | 6.4 | 0.18 | rectangular |
| I-35 | Polymer 35 (80) | PAG 1 (2) | | TBA (0.125) | PGMEA (600) | 6.1 | 0.18 | rectangular |
| I-36 | Polymer 36 (80) | PAG 1 (2) | | TBA (0.125) | PGMEA (600) | 6.0 | 0.18 | rectangular |
| I-37 | Polymer 37 (80) | PAG 1 (2) | | TBA (0.125) | PGMEA (600) | 6.2 | 0.18 | rectangular |
| I-38 | Polymer 38 (80) | PAG 1 (2) | | TBA (0.125) | PGMEA (600) | 6.3 | 0.18 | rectangular |
| I-39 | Polymer 39 (80) | PAG 1 (2) | | TBA (0.125) | PGMEA (600) | 6.2 | 0.20 | rectangular |
| I-40 | Polymer 40 (80) | PAG 1 (2) | | TBA (0.125) | PGMEA (600) | 6.2 | 0.20 | rectangular |
| I-41 | Polymer 41 (80) | PAG 1 (2) | | TBA (0.125) | PGMEA (600) | 6.1 | 0.20 | rectangular |
| I-42 | Polymer 42 (80) | PAG 1 (2) | | TBA (0.125) | PGMEA (600) | 5.7 | 0.18 | rectangular |
| I-43 | Polymer 43 (80) | PAG 1 (2) | | TBA (0.125) | PGMEA (600) | 6.4 | 0.20 | rectangular |
| I-44 | Polymer 44 (80) | PAG 1 (2) | | TBA (0.125) | PGMEA (600) | 5.7 | 0.18 | rectangular |
| I-45 | Polymer 45 (80) | PAG 1 (2) | | TBA (0.125) | PGMEA (600) | 6.3 | 0.18 | rectangular |
| I-46 | Polymer 46 (80) | PAG 1 (2) | | TBA (0.125) | PGMEA (600) | 6.0 | 0.18 | rectangular |
| I-47 | Polymer 47 (80) | PAG 1 (2) | | TBA (0.125) | PGMEA (600) | 6.6 | 0.20 | rectangular |
| I-48 | Polymer 48 (80) | PAG 1 (2) | | TBA (0.125) | PGMEA (600) | 5.9 | 0.18 | rectangular |
| I-49 | Polymer 17 (80) | PAG 1 (2) | | TEA (0.125) | PG/EL (600) | 6.5 | 0.15 | rectangular |
| I-50 | Polymer 17 (80) | PAG 2 (2) | | TEA (0.125) | PG/EL (600) | 3.7 | 0.15 | rectangular |
| I-51 | Polymer 17 (80) | PAG 3 (2) | | TEA (0.125) | PG/EL (600) | 6.4 | 0.15 | rectangular |
| I-52 | Polymer 17 (80) | PAG 4 (2) | | TEA (0.125) | PG/EL (600) | 6.3 | 0.18 | rectangular |
| I-53 | Polymer 17 (80) | PAG 5 (2) | | TEA (0.125) | PG/EL (600) | 6.2 | 0.18 | rectangular |

TABLE 1-continued

| Example | Base resin | Photoacid generator | Dissolution inhibitor | Basic compound | Solvent | Sensitivity | Resolution | Shape |
|---|---|---|---|---|---|---|---|---|
| I-54 | Polymer 17 (80) | PAG 6 (2) | | TEA (0.125) | PG/EL (600) | 6.2 | 0.18 | rectangular |
| I-55 | Polymer 17 (80) | PAG 7 (2) | | TEA (0.125) | PG/EL (600) | 4.0 | 0.15 | rectangular |
| I-56 | Polymer 17 (80) | PAG 8 (2) | | TEA (0.125) | PG/EL (600) | 3.3 | 0.15 | rectangular |
| I-57 | Polymer 24 (80) | PAG 8 (2) | | TBA (0.125) | PGMEA (600) | 3.5 | 0.18 | rectangular |
| I-58 | Polymer 24 (80) | PAG 8 (2) | | TEA (0.125) | PGMEA (600) | 3.7 | 0.15 | rectangular |
| I-59 | Polymer 24 (80) | PAG 8 (2) | | TMMEA (0.125) | PGMEA (600) | 3.2 | 0.18 | rectangular |
| I-60 | Polymer 24 (80) | PAG 8 (2) | | TMEMEA (0.125) | PGMEA (600) | 3.0 | 0.18 | rectangular |
| I-61 | Polymer 29 (80) | PAG 8 (2) | | TBA (0.125) | PGMEA (600) | 3.9 | 0.18 | rectangular |
| I-62 | Polymer 29 (80) | PAG 8 (2) | | TEA (0.125) | PGMEA (600) | 4.0 | 0.15 | rectangular |
| I-63 | Polymer 29 (80) | PAG 8 (2) | | TMMEA (0.125) | PGMEA (600) | 3.8 | 0.15 | rectangular |
| I-64 | Polymer 29 (80) | PAG 8 (2) | | TMEMEA (0.125) | PGMEA (600) | 3.7 | 0.15 | rectangular |
| I-65 | Polymer 32 (80) | PAG 8 (2) | DRR 1 (4) | TBA (0.125) | PGMEA (600) | 4.1 | 0.18 | some positive taper |
| I-66 | Polymer 32 (80) | PAG 8 (2) | DRR 2 (4) | TBA (0.125) | PGMEA (600) | 4.0 | 0.18 | some positive taper |
| I-67 | Polymer 32 (80) | PAG 8 (2) | DRR 3 (4) | TBA (0.125) | PGMEA (600) | 4.0 | 0.18 | some positive taper |
| I-68 | Polymer 32 (80) | PAG 8 (2) | DRR 4 (4) | TBA (0.125) | PGMEA (600) | 3.4 | 0.15 | rectangular |
| I-69 | Polymer 33 (80) | PAG 2 (1) PAG 8 (1) | | TBA (0.125) | PGMEA (600) | 3.0 | 0.15 | rectangular |
| I-70 | Polymer 36 (80) | PAG 2 (1) PAG 8 (1) | | TBA (0.125) | PGMEA (600) | 3.2 | 0.15 | rectangular |
| I-71 | Polymer 35 (80) | PAG 8 (2) | ACC 1 (6) | TBA (0.125) | PGMEA (600) | 3.0 | 0.18 | rectangular |
| I-72 | Polymer 36 (80) | PAG 8 (2) | ACC 1 (6) | TBA (0.125) | PGMEA (600) | 3.1 | 0.18 | rectangular |
| I-73 | Polymer 31 (40) Polymer 38 (40) | PAG 8 (2) | | TEA (0.125) | PGMEA (600) | 3.3 | 0.15 | rectangular |
| I-74 | Polymer 31 (40) Polymer 40 (40) | PAG 8 (2) | | TEA (0.125) | PGMEA (600) | 3.1 | 0.15 | rectangular |
| I-75 | Polymer 20 (40) Polymer 49 (40) | PAG 8 (2) | | TEA (0.125) | PGMEA (600) | 3.6 | 0.18 | rectangular |
| I-76 | Polymer 20 (40) Polymer 50 (40) | PAG 8 (2) | | TEA (0.125) | PGMEA (600) | 4.0 | 2.0 | rectangular |
| I-77 | Polymer 20 (40) Polymer 51 (40) | PAG 8 (2) | | TEA (0.125) | PGMEA (600) | 3.8 | 0.18 | rectangular |
| I-78 | Polymer 20 (40) Polymer 52 (40) | PAG 8 (2) | | TEA (0.125) | PGMEA (600) | 4.2 | 0.20 | rectangular |
| I-79 | Polymer 20 (40) Polymer 53 (40) | PAG 8 (2) | | TEA (0.125) | PGMEA (600) | 3.3 | 0.20 | rectangular |

TABLE 1-continued

| Example | Base resin | Photoacid generator | Dissolution inhibitor | Basic compound | Solvent | Sensitivity | Resolution | Shape |
|---|---|---|---|---|---|---|---|---|
| I-80 | Polymer 20 (40) Polymer 54 (40) | PAG 8 (2) | | TEA (0.125) | PGMEA (600) | 3.5 | 0.18 | rectangular |
| I-81 | Polymer 20 (40) Polymer 55 (40) | PAG 8 (2) | | TEA (0.125) | PGMEA (600) | 3.4 | 0.20 | rectangular |
| I-82 | Polymer 20 (40) Polymer 56 (40) | PAG 8 (2) | | TEA (0.125) | PGMEA (600) | 3.7 | 0.18 | rectangular |

It is seen from Table 1 that the polymers comprising units of the ester compounds within the scope of the invention are highly reactive with acids and ensure that resist materials have a very high sensitivity and resolution.

Example II

Polymers 1 to 48 obtained in the above Synthetic Examples were examined for etching resistance.

Examples II-1 to II-48: Evaluation of polymers' etching resistance

Each of Polymers 1 to 48 obtained in Synthetic Examples and a comparative polymer (polymethyl methacrylate, molecular weight 10,000) was dissolved in cyclohexanone, and spin coated onto a silicon wafer to a thickness of 1.0 μm. The coating was baked on a hot plate at 110° C. for 90 seconds. These coatings were etched with a chlorine-base gas or a fluorine-base gas while the etching rate (Å/min) was measured.

The results are shown in Table 2 while the settings of the instrument are shown in Table 3.

TABLE 2

| Example | Resin | Solvent | Chlorine etching | Fluorine etching |
|---|---|---|---|---|
| II-1 | Polymer 1 (80) | cyclohexanone (480) | 1720 | 1740 |
| II-2 | Polymer 2 (80) | cyclohexanone (480) | 1720 | 1740 |
| II-3 | Polymer 3 (80) | cyclohexanone (480) | 1700 | 1720 |
| II-4 | Polymer 4 (80) | cyclohexanone (480) | 1700 | 1720 |
| II-5 | Polymer 5 (80) | cyclohexanone (480) | 1720 | 1740 |
| II-6 | Polymer 6 (80) | cyclohexanone (480) | 1700 | 1720 |
| II-7 | Polymer 7 (80) | cyclohexanone (480) | 1780 | 1800 |
| II-8 | Polymer 8 (80) | cyclohexanone (480) | 1780 | 1800 |
| II-9 | Polymer 9 (80) | cyclohexanone (480) | 1720 | 1740 |
| II-10 | Polymer 10 (80) | cyclohexanone (480) | 1700 | 1720 |
| II-11 | Polymer 11 (80) | cyclohexanone (480) | 1680 | 1700 |
| II-12 | Polymer 12 (80) | cyclohexanone (480) | 1680 | 1700 |
| II-13 | Polymer 13 (80) | cyclohexanone (480) | 1660 | 1680 |
| II-14 | Polymer 14 (80) | cyclohexanone (480) | 1660 | 1680 |
| II-15 | Polymer 15 (80) | cyclohexanone (480) | 1640 | 1680 |
| II-16 | Polymer 16 (80) | cyclohexanone (480) | 1640 | 1660 |
| II-17 | Polymer 17 (80) | cyclohexanone (480) | 1640 | 1660 |
| II-18 | Polymer 18 (80) | cyclohexanone (480) | 1640 | 1660 |
| II-19 | Polymer 19 (80) | cyclohexanone (480) | 1640 | 1660 |
| II-20 | Polymer 20 (80) | cyclohexanone (480) | 1620 | 1640 |
| II-21 | Polymer 21 (80) | cyclohexanone (480) | 1640 | 1660 |
| II-22 | Polymer 22 (80) | cyclohexanone (480) | 1720 | 1740 |
| II-23 | Polymer 23 (80) | cyclohexanone (480) | 1740 | 1760 |
| II-24 | Polymer 24 (80) | cyclohexanone (480) | 1720 | 1740 |
| II-25 | Polymer 25 (80) | cyclohexanone (480) | 1720 | 1740 |
| II-26 | Polymer 26 (80) | cyclohexanone (480) | 1740 | 1740 |
| II-27 | Polymer 27 (80) | cyclohexanone (480) | 1640 | 1660 |
| II-28 | Polymer 28 (80) | cyclohexanone (480) | 1620 | 1640 |
| II-29 | Polymer 29 (80) | cyclohexanone (480) | 1640 | 1660 |
| II-30 | Polymer 30 (80) | cyclohexanone (480) | 1620 | 1640 |
| II-31 | Polymer 31 (80) | cyclohexanone (480) | 1660 | 1680 |
| II-32 | Polymer 32 (80) | cyclohexanone (480) | 1680 | 1700 |
| II-33 | Polymer 33 (80) | cyclohexanone (480) | 1680 | 1700 |
| II-34 | Polymer 34 (80) | cyclohexanone (480) | 1700 | 1720 |
| II-35 | Polymer 35 (80) | cyclohexanone (480) | 1740 | 1760 |
| II-36 | Polymer 36 (80) | cyclohexanone (480) | 1740 | 1760 |
| II-37 | Polymer 37 (80) | cyclohexanone (480) | 1640 | 1660 |
| II-38 | Polymer 38 (80) | cyclohexanone (480) | 1620 | 1660 |
| II-39 | Polymer 39 (80) | cyclohexanone (480) | 1700 | 1720 |
| II-40 | Polymer 40 (80) | cyclohexanone (480) | 1700 | 1720 |
| II-41 | Polymer 41 (80) | cyclohexanone (480) | 1560 | 1580 |
| II-42 | Polymer 42 (80) | cyclohexanone (480) | 1560 | 1580 |
| II-43 | Polymer 43 (80) | cyclohexanone (480) | 1560 | 1580 |
| II-44 | Polymer 44 (80) | cyclohexanone (480) | 1560 | 1580 |
| II-45 | Polymer 45 (80) | cyclohexanone (480) | 1580 | 1600 |
| II-46 | Polymer 46 (80) | cyclohexanone (480) | 1580 | 1600 |
| II-47 | Polymer 47 (80) | cyclohexanone (480) | 1580 | 1600 |
| II-48 | Polymer 48 (80) | cyclohexanone (480) | 1560 | 1600 |
| Comparison | polymethyl methacrylate (80) | cyclohexanone (480) | 2500 | 2250 |

TABLE 3

| | Chlorine etching | Fluorine etching |
|---|---|---|
| Manufacturer | Nichiden Anerba K.K. | Tokyo Electron K.K. |
| Model | L451D | TE8500 |
| Gas/flow rate | $Cl_2$/20 sccm $O_2$/2 sccm $CHF_3$/15 sccm $BCl_3$/100 sccm | $CHF_3$/7 sccm $CF_4$/45 sccm $O_2$/20 sccm Ar/90 sccm |
| RF power | 300 W | 600 W |
| Pressure | 2 Pa | 450 mTorr |
| Temperature | 23° C. | −20° C. |
| Time | 360 sec | 60 sec |

It is seen from Table 2 that the polymers within the scope of the invention are highly resistant to etching.

Japanese Patent Application Nos. 145080/1998 and 292575/1998 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ester compound of the following general formula (1)

wherein $R^1$ is hydrogen, methyl or $CH_2CO_2R^4$; $R^2$ is hydrogen, methyl or $CO_2R^4$; $R^3$ is a straight, branched or cyclic alkyl group of 1 to 8 carbon atoms or a substituted or unsubstituted aryl group of 6 to 20 carbon atoms; $R^4$ is a straight, branched or cyclic alkyl group of 1 to 15 carbon atoms; k is equal to 0 or 1, m is equal to 0 or 1, n is equal to 0, 1, 2 or 3, and 2m+n is equal to 2 or 3.

2. An ester of compound according to claim 1, wherein $R^3$ is a methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

3. An ester compound according to claim 1, wherein $R^4$ is methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, or butyladamantyl.

4. An ester compound according to claim 2, wherein $R^4$ is methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, or butyladamantyl.

5. An ester compound according to claim 1, wherein $R^1$ is H or $CH_2CO_2CH_3$, $R^2$ is H or $CO_2CH_3$, and $R^3$ is methyl, ethyl, isopropyl, or n-butyl.

6. An ester compound according to claim 1, wherein k is 0.

7. An ester compound according to claim 1, wherein k is 1.

8. An ester compound according to claim 1, wherein n is 2 or 3.

9. An ester compound according to claim 1, wherein m is 0.

10. An ester compound according to claim 1, wherein m is 1.

11. An ester compound according to claim 1, wherein said ester compound is:

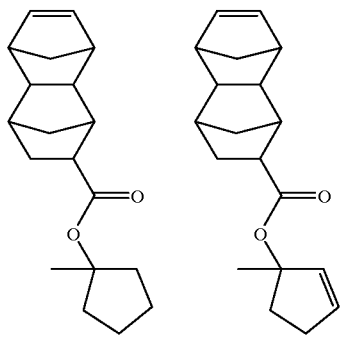

12. An ester of compound according to claim 1, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

13. An ester of compound according to claim 3, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

14. An ester of compound according to claim 5, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

15. An ester of compound according to claim 6, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

16. An ester of compound according to claim 7, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

17. An ester of compound according to claim 8, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

18. An ester of compound according to claim 9, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

19. An ester of compound according to claim 10, wherein $R^3$ is ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, phenyl, methylphenyl, naphthyl, anthryl, phenanthryl, or pyrenyl.

20. An ester compound according to claim 1, wherein said ester compound is:

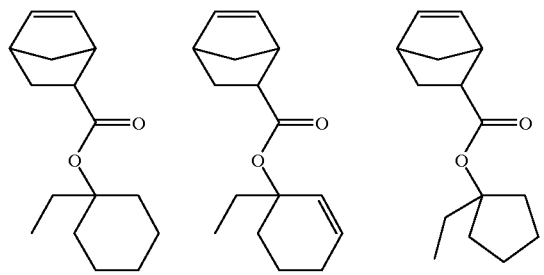

* * * * *